US009276222B2

(12) United States Patent
Inoue et al.

(10) Patent No.: US 9,276,222 B2
(45) Date of Patent: Mar. 1, 2016

(54) ORGANOMETALLIC IRIDIUM COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Miki Kanamoto, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/313,294

(22) Filed: Jun. 24, 2014

(65) Prior Publication Data

US 2015/0005496 A1   Jan. 1, 2015

(30) Foreign Application Priority Data

Jun. 28, 2013   (JP) .................. 2013-136143

(51) Int. Cl.
| | | |
|---|---|---|
| H01L 51/00 | (2006.01) | |
| C07F 15/00 | (2006.01) | |
| C09K 11/06 | (2006.01) | |
| H01L 51/50 | (2006.01) | |

(52) U.S. Cl.
CPC ............ *H01L 51/0085* (2013.01); *C07F 15/00* (2013.01); *C09K 11/06* (2013.01); *C09K 2211/1007* (2013.01); *C09K 2211/1029* (2013.01); *C09K 2211/1044* (2013.01); *C09K 2211/1059* (2013.01); *C09K 2211/185* (2013.01); *H01L 51/5016* (2013.01)

(58) Field of Classification Search
CPC .................................................. H01L 51/0085
See application file for complete search history.

(56) References Cited

U.S. PATENT DOCUMENTS

| | | |
|---|---|---|
| 6,097,147 A | 8/2000 | Baldo et al. |
| 6,830,828 B2 | 12/2004 | Thompson et al. |
| 6,902,830 B2 | 6/2005 | Thompson et al. |
| 6,974,639 B2 | 12/2005 | Tsuboyama et al. |
| 7,001,536 B2 | 2/2006 | Thompson et al. |
| 7,220,495 B2 | 5/2007 | Tsuboyama et al. |
| 7,291,406 B2 | 11/2007 | Thompson et al. |
| 7,354,662 B2 | 4/2008 | Tsuboyama et al. |
| 7,537,844 B2 | 5/2009 | Thompson et al. |
| 7,807,839 B2 | 10/2010 | Inoue et al. |
| 7,883,787 B2 | 2/2011 | Thompson et al. |
| 2005/0221123 A1 | 10/2005 | Inoue et al. |
| 2007/0129545 A1 | 6/2007 | Inoue et al. |
| 2007/0244320 A1 | 10/2007 | Inoue et al. |
| 2009/0015143 A1 | 1/2009 | Inoue et al. |
| 2009/0039776 A1 | 2/2009 | Yamada et al. |
| 2010/0105902 A1 | 4/2010 | Inoue et al. |
| 2011/0057560 A1 | 3/2011 | Inoue et al. |
| 2011/0082296 A1 | 4/2011 | Inoue et al. |
| 2011/0112296 A1 | 5/2011 | Thompson et al. |
| 2012/0061707 A1 | 3/2012 | Seo et al. |
| 2012/0098417 A1 | 4/2012 | Inoue et al. |
| 2012/0208999 A1 | 8/2012 | Konno |
| 2013/0165653 A1 | 6/2013 | Inoue et al. |

FOREIGN PATENT DOCUMENTS

| | | |
|---|---|---|
| EP | 1 239 526 A2 | 9/2002 |
| EP | 2 429 008 A1 | 3/2012 |
| JP | 2002-332292 A | 11/2002 |
| JP | 2003-109758 A | 4/2003 |
| JP | 2006-120905 A | 5/2006 |
| JP | 2007-137872 | 6/2007 |
| JP | 2008-069221 | 3/2008 |
| JP | 2012-149030 A | 8/2012 |
| TW | I231157 B | 4/2005 |
| WO | WO 00/70655 A2 | 11/2000 |
| WO | WO 2008/035664 A1 | 3/2008 |
| WO | WO 2011/024737 A1 | 3/2011 |
| WO | WO 2012/053627 A1 | 4/2012 |

OTHER PUBLICATIONS

Niu, Y.-H. et al., "Highly Efficient Red Electrophosphorescent Devices Based on an Iridium Complex with Triflouromethyl-Substituted Pyrimidine Ligand," Applied Physics Letters, Aug. 30, 2004, vol. 85, No. 9, pp. 1619-1621.

Caygill,G.B. et al., "Cyclometallated Compounds IV. Cyclopalladation of Phenylpyrimidines and X-Ray Structure of a Doubly Cyclopalladated Derivative of 4,6-diphenylpyrimidine," Journal of Organometallic Chemistry, Feb. 13, 1990, vol. 382, No. 3, pp. 455-469.

Kawanishi,Y. et al., "Dependence of Spectroscopic, Electrochemical, and Excited-State Properties of Tris Chelate Ruthenium(II) Complexes on Ligand Structure," Inorganic Chemistry, 1989, vol. 28, No. 15, pp. 2968-2975.

Kozhevnikov, V.N. et al., "Highly Luminescent Mixed-Metal Pt(II)/Ir(III) Complexes: Bis-Cyclometalation of 4,6-Diphenylpyrimidine as a Versatile Route to Rigid Multimetallic Assemblies," Inorganic Chemistry, 2011, vol. 50, No. 13, pp. 6304-6313.

Bredereck, H. et al., "Formamide Reactions, VIII. A New Pyrimidine-Synthesis," Chem.Ber. (Chemische Berichte), 1957, vol. 90, pp. 942-952.

*Primary Examiner* — Brian McDowell
(74) *Attorney, Agent, or Firm* — Husch Blackwell LLP

(57) ABSTRACT

Provided as a novel substance is a long-lifetime organometallic iridium complex emitting yellow light with high emission efficiency. The organometallic iridium complex is represented by General Formula (G1) and has a structure in which a phenyl group whose 2-position and 6-position are each substituted by an alkyl group is bonded to the 4-position of pyrimidine. In General Formula (G1), $R^1$ and $R^2$ each independently represent a substituted or unsubstituted alkyl group having 1 to 6 carbon atoms.

(G1)

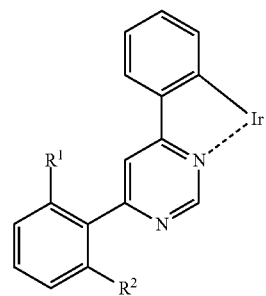

11 Claims, 13 Drawing Sheets

ORGANOMETALLIC IRIDIUM COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to an organometallic iridium complex, particularly to an organometallic iridium complex capable of converting triplet excitation energy into luminescence. In addition, the present invention relates to a light-emitting element, a light-emitting device, an electronic device, and a lighting device each including the organometallic iridium complex.

2. Description of the Related Art

Organic compounds are brought into an excited state by absorption of light. Through this excited state, various reactions (photochemical reactions) are caused in some cases, or luminescence is generated in some cases. Therefore, the organic compounds have a wide range of applications.

As one example of the photochemical reactions, a reaction of singlet oxygen with an unsaturated organic molecule (oxygen addition) is known. Since the ground state of an oxygen molecule is a triplet state, oxygen in a singlet state (singlet oxygen) is not generated by direct photoexcitation. However, in the presence of another triplet excited molecule, singlet oxygen is generated to cause an oxygen addition reaction. In this case, a compound capable of forming the triplet excited molecule is referred to as a photosensitizer.

As described above, for generation of singlet oxygen, a photosensitizer capable of forming a triplet excited molecule by photoexcitation is needed. However, the ground state of an ordinary organic compound is a singlet state; therefore, photoexcitation to a triplet excited state is forbidden transition and generation of a triplet excited molecule is difficult. A compound that can easily cause intersystem crossing from the singlet excited state to the triplet excited state (or a compound that allows the forbidden transition of photoexcitation directly to the triplet excited state) is thus required as such a photosensitizer. In other words, such a compound can be used as the photosensitizer and is often useful.

The above compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting energy in the triplet excited state into luminescence (hereinafter, referred to as a phosphorescent compound), include a light-emitting element including an organic compound as a light-emitting substance.

This light-emitting element has a simple structure in which a light-emitting layer including an organic compound that is a light-emitting substance is provided between electrodes. This light-emitting element has attracted attention as a next-generation flat panel display element in terms of characteristics such as being thin and light in weight, high speed response, and direct current low voltage driving. Further, a display device including this light-emitting element is superior in contrast, image quality, and wide viewing angle.

The light-emitting element including an organic compound as a light-emitting substance has a light emission mechanism that is of a carrier injection type: a voltage is applied between electrodes where a light-emitting layer is interposed, electrons and holes injected from the electrodes recombine to put the light-emitting substance into an excited state, and then light is emitted in returning from the excited state to the ground state. As in the case of photoexcitation described above, types of the excited state include a singlet excited state (S*) and a triplet excited state (T*). The statistical generation ratio thereof in the light-emitting element is considered to be S*:T*=1:3.

At room temperature, a compound capable of converting energy in a singlet excited state into luminescence (hereinafter, referred to as a fluorescent compound) exhibits only luminescence from the singlet excited state (fluorescence), not luminescence from the triplet excited state (phosphorescence). Accordingly, the internal quantum efficiency (the ratio of the number of generated photons to the number of injected carriers) of a light-emitting element including the fluorescent compound is thought to have a theoretical limit of 25%, on the basis of S*:T*=1:3.

On the other hand, in a case of a light-emitting element including the phosphorescent compound described above, the internal quantum efficiency thereof can be improved to 75% to 100% in theory; namely, the emission efficiency thereof can be 3 to 4 times as much as that of the light-emitting element including a fluorescent compound. Therefore, the light-emitting element including a phosphorescent compound has been actively developed in recent years in order to achieve a highly efficient light-emitting element. An organometallic iridium complex that contains iridium or the like as a central metal is particularly attracting attention as a phosphorescent compound because of its high phosphorescence quantum yield (refer to Patent Documents 1, Patent Document 2, and Patent Document 3).

REFERENCE

Patent Document

[Patent Document 1] Japanese Published Patent Application No. 2007-137872
[Patent Document 2] Japanese Published Patent Application No. 2008-069221
[Patent Document 3] International Publication WO 2008/035664 Pamphlet

SUMMARY OF THE INVENTION

Although phosphorescent materials exhibiting various emission colors have been actively developed as disclosed in Patent Documents 1 to 3, development of novel materials with higher efficiency has been desired.

In view of the above, one embodiment of the present invention provides a long-lifetime organometallic iridium complex emitting yellow light with high emission efficiency, as a novel substance. Another embodiment of the present invention provides a light-emitting element, a light-emitting device, an electronic device, or a lighting device with high emission efficiency.

One embodiment of the present invention is an organometallic iridium complex including a ligand with a structure in which a phenyl group whose 2-position and 6-position are each substituted by an alkyl group is bonded to the 4-position of pyrimidine. Accordingly, one embodiment of the present invention is an organometallic iridium complex having a structure represented by General Formula (G1).

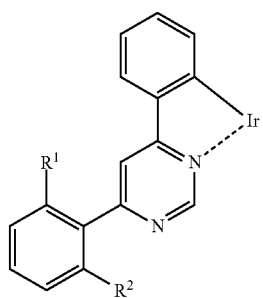
(G1)

In General Formula (G1), $R^1$ and $R^2$ each independently represent a substituted or unsubstituted alkyl group having 1 to 6 carbon atoms.

Another embodiment of the present invention is an organometallic iridium complex represented by General Formula (G2).

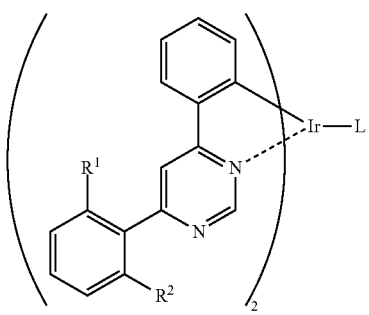
(G2)

In General Formula (G2), $R^1$ and $R^2$ each independently represent a substituted or unsubstituted alkyl group having 1 to 6 carbon atoms; and L represents a monoanionic ligand.

In General Formula (G2), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two coordinating elements are both nitrogen. A monoanionic bidentate chelate ligand having a beta-diketone structure is particularly preferable.

The monoanionic ligand is preferably a ligand represented by any of General Formulae (L1) to (L7).

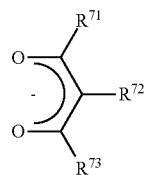
(L1)

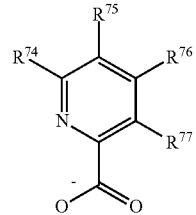
(L2)

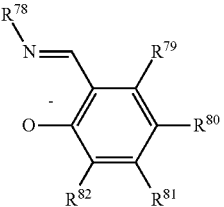
(L3)

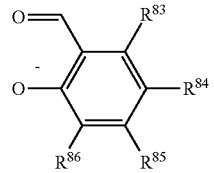
(L4)

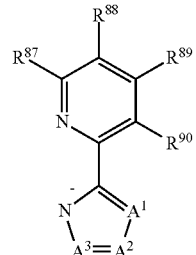
(L5)

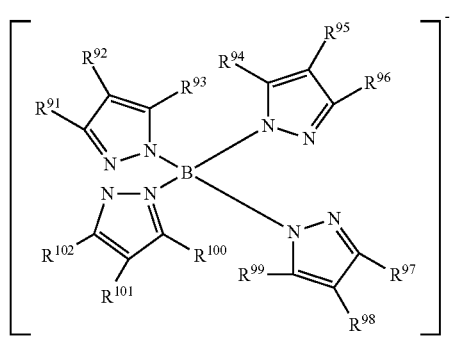
(L6)

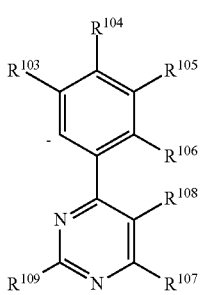
(L7)

In the formulae, $R^{71}$ to $R^{109}$ each individually represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. In addition, $A^1$ to $A^3$ each individually represent any of nitrogen, $sp^2$ hybridized carbon bonded to hydrogen, and $sp^2$ carbon having a substituent. The substituent represents any of an alkyl group having 1 to 6 carbon atoms, a halogen group, a haloalkyl group having 1 to 6 carbon atoms, and a phenyl group.

Another embodiment of the present invention is an organometallic iridium complex represented by General Formula (G3).

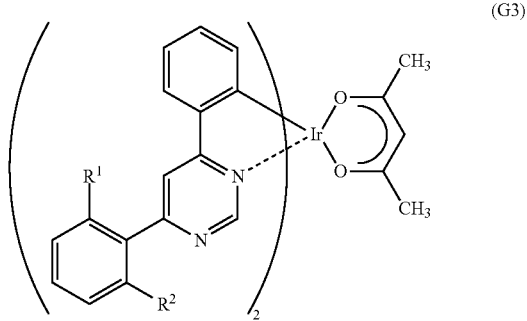

(G3)

In General Formula (G3), $R^1$ and $R^2$ each independently represent a substituted or unsubstituted alkyl group having 1 to 6 carbon atoms.

Another embodiment of the present invention is an organometallic iridium complex represented by General Formula (G4).

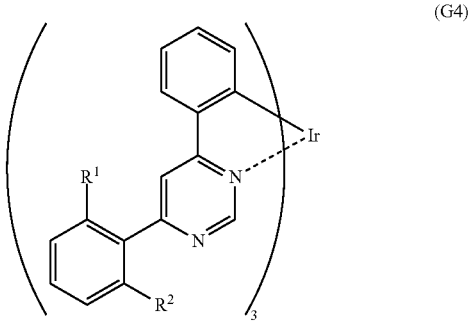

(G4)

In General Formula (G4), $R^1$ and $R^2$ each independently represent a substituted or unsubstituted alkyl group having 1 to 6 carbon atoms.

Another embodiment of the present invention is an organometallic iridium complex represented by Structural Formula (100).

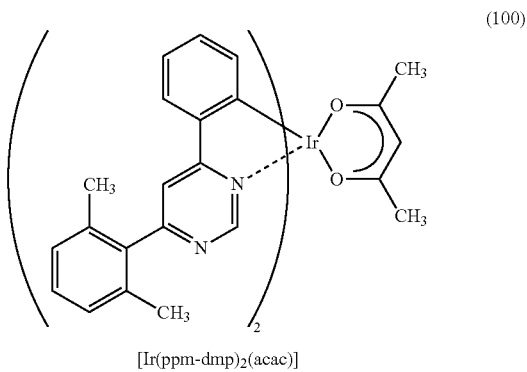

(100)

[Ir(ppm-dmp)$_2$(acac)]

Further, the organometallic iridium complex of one embodiment of the present invention is very effective for the following reason: the organometallic iridium complex can emit phosphorescence, that is, it can provide luminescence from a triplet excited state and can exhibit emission, and therefore higher efficiency is possible when the organometallic iridium complex is applied to a light-emitting element. Thus, one embodiment of the present invention also includes a light-emitting element in which the organometallic iridium complex of one embodiment of the present invention is used.

Other embodiments of the present invention are not only a light-emitting device including the light-emitting element but also a lighting device each including the light-emitting device. The light-emitting device in this specification refers to an image display device and a light source (e.g., a lighting device). In addition, the light-emitting device includes, in its category, all of a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

One embodiment of the present invention can provide a long-lifetime organometallic iridium complex emitting yellow light (emission wavelength: approximately 555 nm) with high emission efficiency, as a novel substance. With the use of the novel organometallic iridium complex, a light-emitting element, a light-emitting device, an electronic device, or a lighting device with high efficiency and/or low power consumption can be provided.

DETAILED DESCRIPTION OF THE INVENTION

Figure 1:
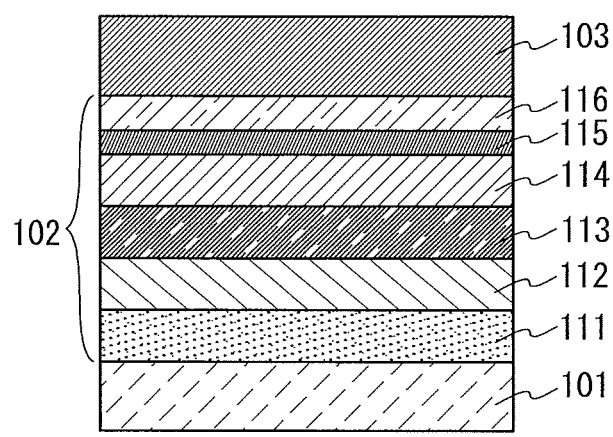
FIG. 1 illustrates a structure of a light-emitting element.

Hereinafter, embodiments of the present invention will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments.

(Embodiment 1)

In this embodiment, organometallic iridium complexes which are embodiments of the present invention are described.

An organometallic iridium complex of one embodiment of the present invention includes a ligand with a structure in which a phenyl group whose 2-position and 6-position are each substituted by an alkyl group is bonded to the 4-position of pyrimidine. An organometallic iridium complex of one embodiment of the present invention described in this embodiment has a structure represented by General Formula (G2).

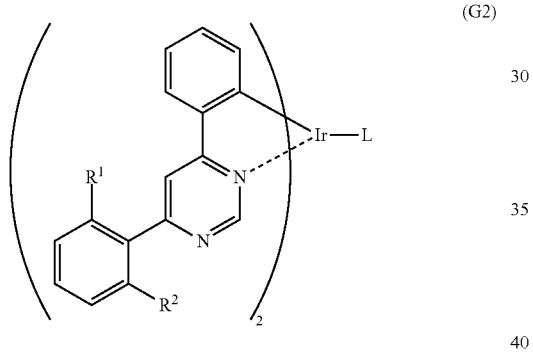

(G2)

In General formula (G2), $R^1$ and $R^2$ each independently represent a substituted or unsubstituted alkyl group having 1 to 6 carbon atoms; and L represents a monoanionic ligand.

In General Formula (G2), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two coordinating elements are both nitrogen. A monoanionic bidentate chelate ligand having a beta-diketone structure is particularly preferable.

The monoanionic ligand is preferably a ligand represented by any of General Formulae (L1) to (L7).

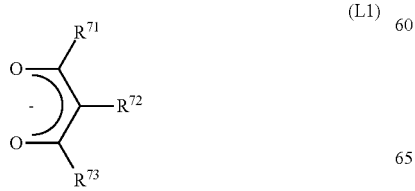

(L1)

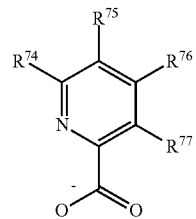

(L2)

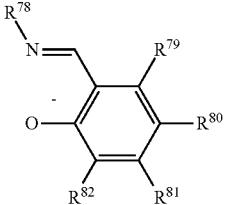

(L3)

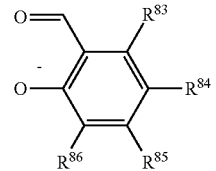

(L4)

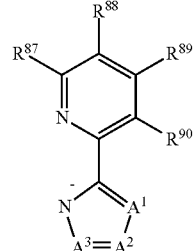

(L5)

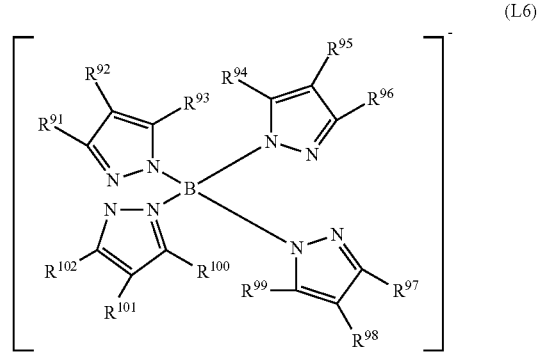

(L6)

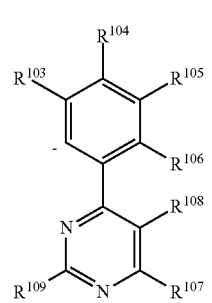

(L7)

In the formulae, $R^{71}$ to $R^{109}$ each individually represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. In addition, $A^1$ to $A^3$ each individually represent any of nitrogen, $sp^2$ hybridized carbon bonded to hydrogen, and $sp^2$ carbon having a substituent. The substituent represents any of an alkyl group having 1 to 6 carbon atoms, a halogen group, a haloalkyl group having 1 to 6 carbon atoms, and a phenyl group.

Note that specific examples of the substituted or unsubstituted alkyl group having 1 to 6 carbon atoms in $R^1$ and $R^2$ include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Note that the organometallic iridium complex of one embodiment of the present invention has a structure in which a phenyl group whose 2-position and 6-position are each substituted by an alkyl group is bonded to the 4-position of a pyrimidine skeleton. With this structure, a broad electron distribution caused by a conjugated bond between the pyrimidine skeleton and the phenyl group can be prevented; thus, the spectrum derived from the organometallic iridium complex can be narrower than that of an organometallic iridium complex that does not have the above structure. In addition, the emission efficiency can be increased.

Another embodiment of the present invention is an organometallic iridium complex represented by General Formula (G3).

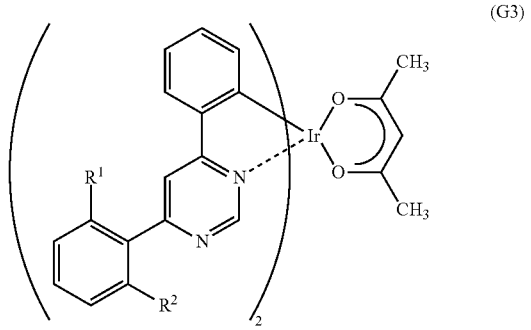

(G3)

In General Formula (G3), $R^1$ and $R^2$ each independently represent a substituted or unsubstituted alkyl group having 1 to 6 carbon atoms.

Another embodiment of the present invention is an organometallic iridium complex represented by General Formula (G4).

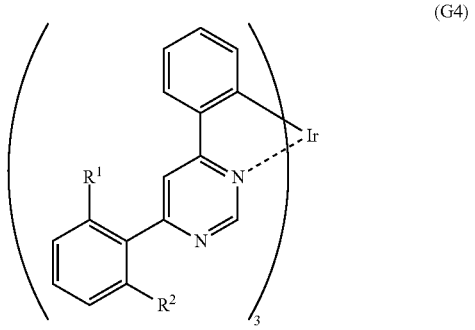

(G4)

In General Formula (G4), $R^1$ and $R^2$ each independently represent a substituted or unsubstituted alkyl group having 1 to 6 carbon atoms.

Next, specific structural formulae of the above-described organometallic iridium complexes each of which is one embodiment of the present invention are shown (Structural Formulae (100) to (111)). Note that the present invention is not limited thereto.

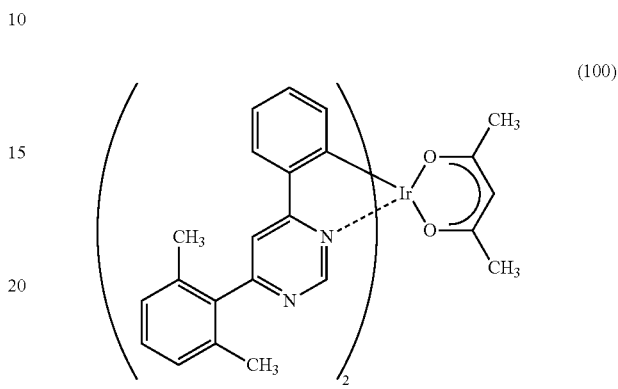

(100)

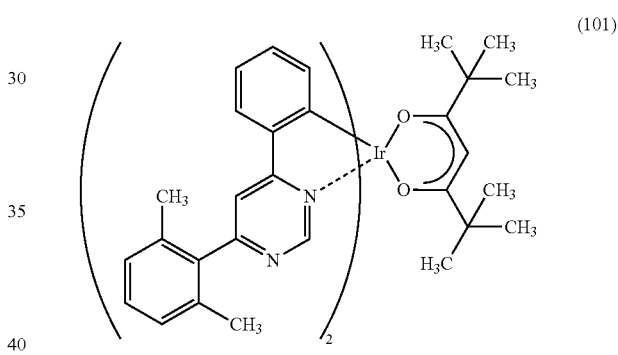

(101)

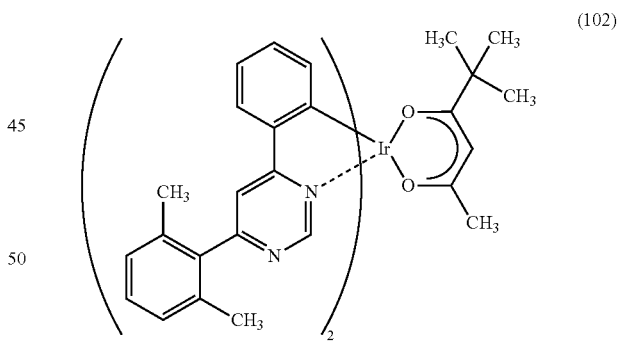

(102)

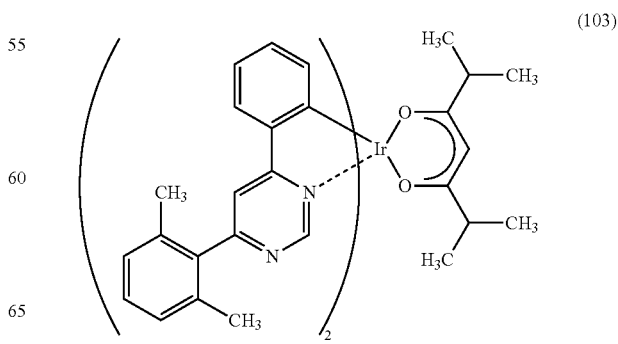

(103)

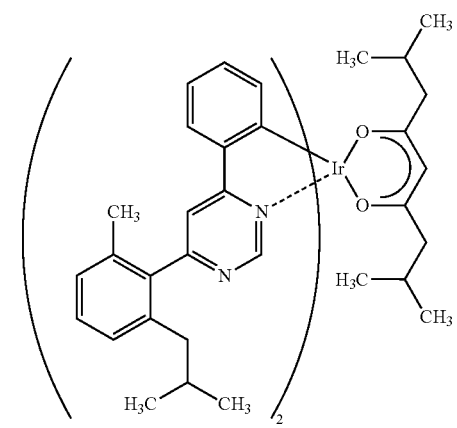
(104)
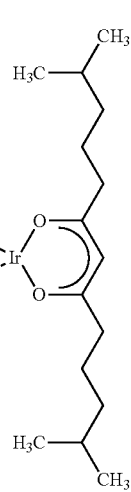
(105)
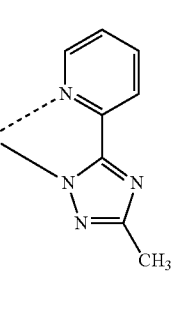
(106)
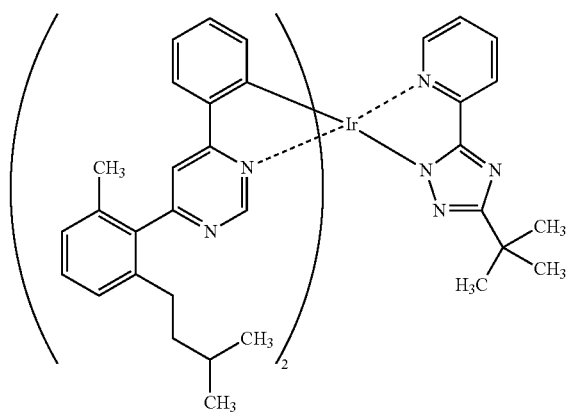
(107)
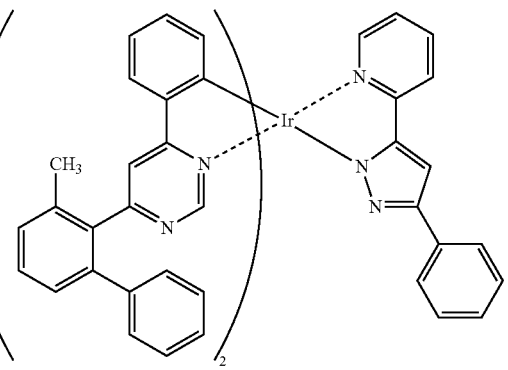
(108)
(109)
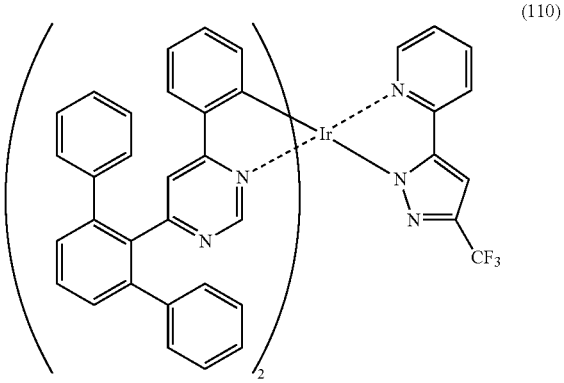
(110)

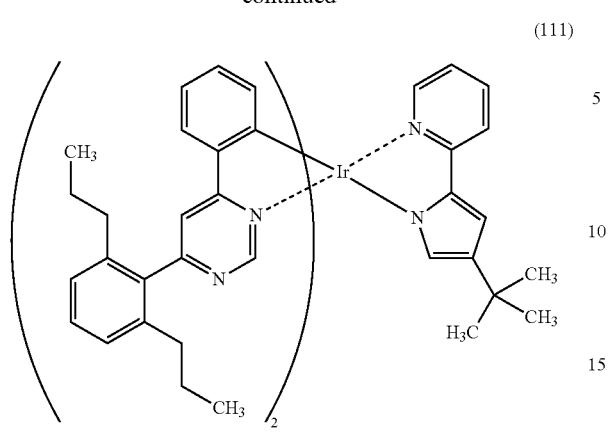

(111)

Note that organometallic iridium complexes represented by Structural Formulae (100) to (111) are novel substances capable of emitting phosphorescence. There can be geometrical isomers and stereoisomers of these substances depending on the type of the ligand. The organometallic iridium complex of one embodiment of the present invention includes all of these isomers.

Next, an example of a method for synthesizing an organometallic iridium complex represented by General Formula (G2) is described.

<<Method for Synthesizing Pyrimidine Derivative Represented by General Formula (G0)>>

First, an example of a method for synthesizing a pyrimidine derivative represented by General Formula (G0) is described.

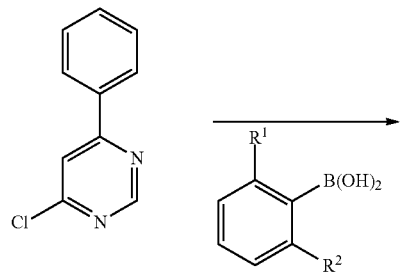

(G0)

In General Formula (G0), $R^1$ and $R^2$ each independently represent a substituted or unsubstituted alkyl group having 1 to 6 carbon atoms.

Synthesis Scheme (A) of the pyrimidine derivative represented by General Formula (G0) is shown below.

(A)

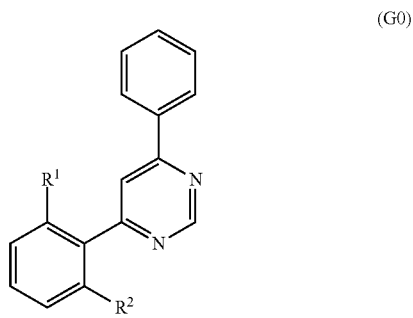

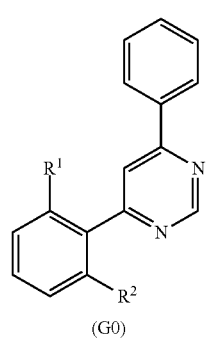

(G0)

In Synthesis Scheme (A), the pyrimidine derivative represented by General Formula (G0) can be synthesized by a coupling reaction using 4-chloro-6-phenylpyrimidine and an aryl boronic acid.

Since the 4-chloro-6-phenylpyrimidine and the aryl boronic acid are commercially available or can be synthesized, many kinds of pyrimidine derivatives represented by General Formula (G0) can be synthesized. Thus, a feature of the organometallic iridium complex of one embodiment of the present invention is the abundance of ligand variations.

<<Method of synthesizing an organometallic iridium complex of one embodiment of the present invention represented by General Formula (G2)>>

Next, a method for synthesizing the organometallic iridium complex of one embodiment of the present invention represented by General Formula (G2), which is formed using the pyrimidine derivative represented by General Formula (G0), is described.

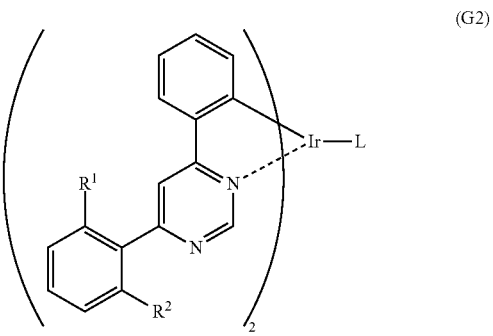

(G2)

In General Formula (G2), $R^1$ and $R^2$ each independently represent a substituted or unsubstituted alkyl group having 1 to 6 carbon atoms; and L represents a monoanionic ligand.

Synthesis Scheme (B) of the organometallic iridium complex represented by General Formula (G2) is shown below.

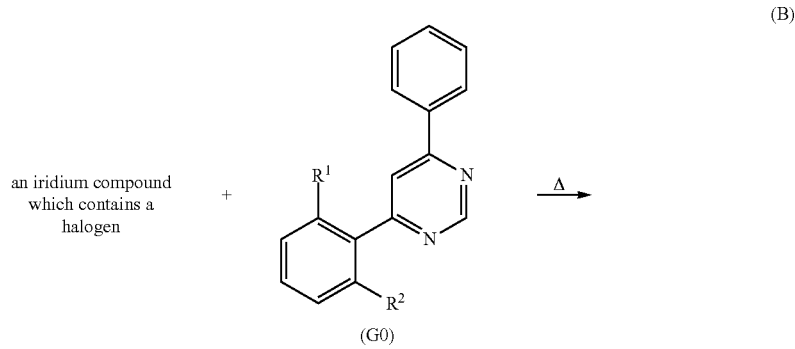

(B)

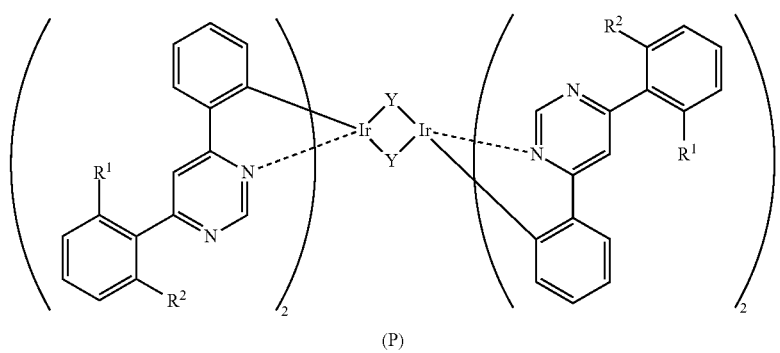

(P)

In Synthesis Scheme (B), $R^1$ and $R^2$ each independently represent a substituted or unsubstituted alkyl group having 1 to 6 carbon atoms; and Y represents halogen.

As shown in Synthesis Scheme (B), a pyrimidine derivative represented by General Formula (G0) and an iridium compound which contains a halogen (e.g., iridium chloride, iridium bromide, or iridium iodide) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby a dinuclear complex (P), which is one type of an organometallic iridium complex including a halogen-bridged structure, can be obtained.

There is no particular limitation on a heating means, and an oil bath, a sand bath, or an aluminum block may be used. Alternatively, microwaves can be used as a heating means.

As shown in Synthesis Scheme (C), the dinuclear complex (P) obtained in Synthesis Scheme (B) is reacted with a ligand HL in an inert gas atmosphere, whereby a proton of the ligand HL is eliminated and a monoanionic ligand L coordinates to the central metal iridium. Thus, the organometallic iridium complex of one embodiment of the present invention represented by General Formula (G2) can be obtained.

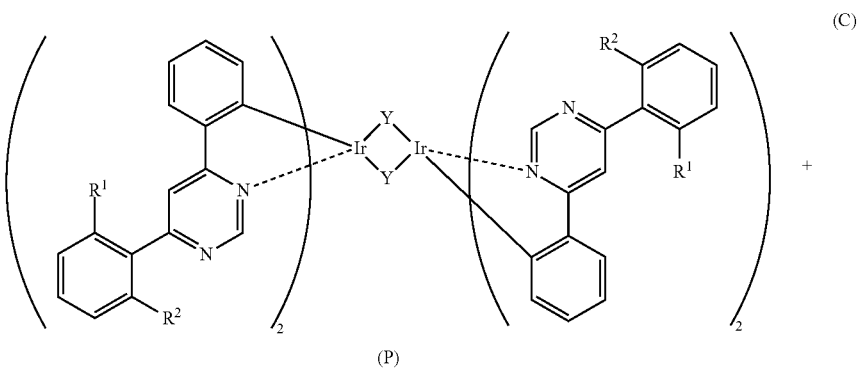

(C)

(P)

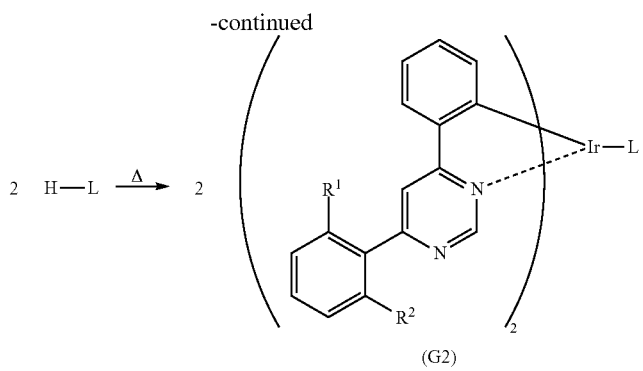

(G2)

In Synthesis Scheme (C), $R^1$ and $R^2$ each independently represent a substituted or unsubstituted alkyl group having 1 to 6 carbon atoms; and L represents a monoanionic ligand.

There is no particular limitation on a heating means, and an oil bath, a sand bath, or an aluminum block may be used. Alternatively, microwaves can be used as a heating means.

The above is the description of the example of a method of synthesizing an organometallic iridium complex of one embodiment of the present invention; however, the present invention is not limited thereto and any other synthesis method may be employed.

The above-described organometallic iridium complex of one embodiment of the present invention can emit phosphorescence and thus can be used as a light-emitting material or a light-emitting substance of a light-emitting element.

With the use of the organometallic iridium complex of one embodiment of the present invention, a light-emitting element, a light-emitting device, an electronic device, or a lighting device with high emission efficiency can be obtained. Alternatively, it is possible to obtain a light-emitting element, a light-emitting device, an electronic device, or a lighting device with low power consumption.

Note that the structure described in this embodiment can be combined as appropriate with any of the structures described in the other embodiments.

(Embodiment 2)

In this embodiment, a light-emitting element in which the organometallic iridium complex described in Embodiment 1 as one embodiment of the present invention is used for a light-emitting layer is described with reference to FIG. 1.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge generation layer (E) 116, and the like in addition to the light-emitting layer 113.

By application of a voltage to such a light-emitting element, holes injected from the first electrode 101 side and electrons injected from the second electrode 103 side recombine in the light-emitting layer 113 to raise the organometallic iridium complex to an excited state. Then, light is emitted when the organometallic iridium complex in the excited state returns to the ground state. Thus, the organometallic iridium complex of one embodiment of the present invention functions as a light-emitting substance in the light-emitting element.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge generation layer (E) 116 is a layer containing a substance having a high hole-transport property and an acceptor substance. Owing to the acceptor substance, electrons are extracted from the substance having a high hole-transport property and the extracted electrons are injected from the electron-injection layer 115 having an electron-injection property into the light-emitting layer 113 through the electron-transport layer 114.

A specific example in which the light-emitting element described in this embodiment is manufactured is described.

For the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance having a high hole-transport property which is used for the hole-injection layer 111, the hole-transport layer 112, and the charge generation layer (E) 116, the following can be given, for example: aromatic amines such as 4,4'-bis[N-(1-naphthyl)-N-phenylamino]biphenyl (abbreviation: NPB or α-NPD), N,N-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. In addition, the following carbazole derivatives and the like can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly ones that have a hole mobility of $10^{-6}$ cm$^2$/Vs or higher. Note that any substance other than the above substances may be used as long as the hole-transport property is higher than the electron-transport property.

Further, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 and the charge generation layer (E) 116, a transition metal oxide or an oxide of a metal belonging to any of Group 4 to Group 8 of the periodic table can be given. Specifically, molybdenum oxide is particularly preferable.

The light-emitting layer 113 contains the organometallic iridium complex described in Embodiment 1 as a guest material serving as a light-emitting substance and a substance that has higher triplet excitation energy than this organometallic iridium complex as a host material.

Preferable examples of the substance (i.e., host material) used for dispersing any of the above-described organometallic iridium complexes include: any of compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Note that in the case where the light-emitting layer 113 contains the above-described organometallic iridium complex (guest material) and the host material, phosphorescence with high emission efficiency can be obtained from the light-emitting layer 113.

The electron-transport layer 114 is a layer containing a substance having a high electron-transport property. For the electron-transport layer 114, metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ cm$^2$/Vs or higher. Note that any substance other than the above substances may be used for the electron-transport layer 114 as long as the electron-transport property is higher than the hole-transport property.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound of any of the above metals such as lithium fluoride (LiF), cesium fluoride (CsF), calcium fluoride (CaF$_2$), or lithium oxide (LiO$_x$) can be used. Alternatively, a rare earth metal compound such as erbium fluoride (ErF$_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the substances for fanning the electron-transport layer 114 (e.g., a metal complex and a heteroaromatic compound), which are described above, or the like can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium or the like can be used. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge generation layer (E) 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic iridium complex and thus can have higher efficiency than a light-emitting element using a fluorescent compound.

Note that the structure described in this embodiment can be combined as appropriate with any of the structures described in the other embodiments.

(Embodiment 3)

In this embodiment, as one embodiment of the present invention, a light-emitting element in which two or more kinds of organic compounds as well as an organometallic iridium complex are used for a light-emitting layer is described.

Figure 2:
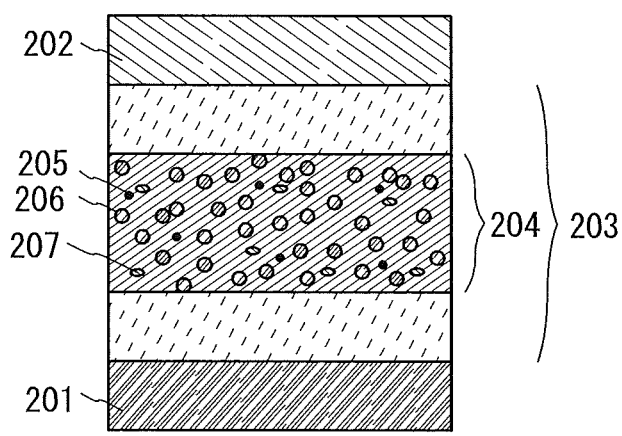
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge generation layer (E), and the like. Note that for the hole-injection layer, the hole-transport layer, the electron-transport layer, the electron-injection layer, and the charge generation layer (E), the substances described in Embodiment 2 can be used.

The light-emitting layer 204 described in this embodiment contains a phosphorescent compound 205 using the organometallic iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. The reason for this is that, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound in order to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound 206 and the second organic compound 207 preferably forms an excited complex (also referred to as exciplex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is presumed to occur.

For the phosphorescent compound 205, the organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As a compound which is likely to accept electrons, for example, 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

As a compound which is likely to accept holes, for example, 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N,N'-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4- diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of one embodiment of the present invention, the light-emitting layer 204 can be formed using a host molecule having a hole-trapping property and a host molecule having an electron-trapping property as the two kinds of organic compounds (the first organic compound 206 and the second organic compound 207) other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

The structure of the light-emitting element described in this embodiment is an example. The light-emitting element of one embodiment of the present invention can have a microcavity structure in addition to the structure.

Note that the structure described in this embodiment can be combined as appropriate with any of the structures described in the other embodiments.

(Embodiment 4)

In this embodiment, as one embodiment of the present invention, a light-emitting element (hereinafter referred to as tandem light-emitting element) in which a charge generation layer is provided between a plurality of EL layers is described.

Figure 3A:
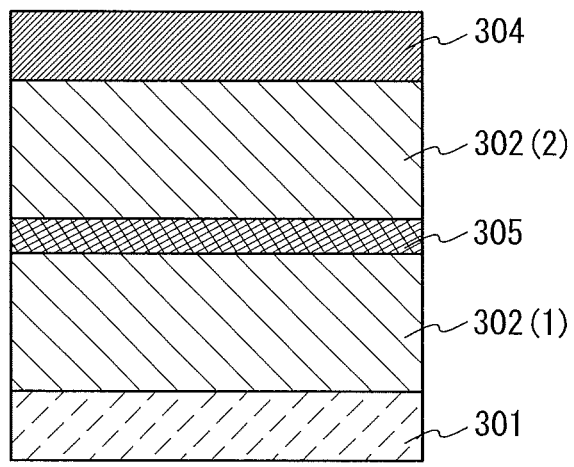
FIGS. 3A and 3B each illustrate a structure of a light-emitting element.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2. In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and can be similar to that of the EL layer described in Embodiment 2 or 3.

Further, a charge generation layer (I) 305 is provided between the plurality of EL layers (the first EL layer 302(1) and the second EL layer 302(2)). The charge generation layer (I) 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer (I) 305 injects electrons into the first EL layer 302(1) and injects holes into the second EL layer 302(2).

Note that in terms of light extraction efficiency, the charge generation layer (I) 305 preferably has a light-transmitting property with respect to visible light (specifically, the charge generation layer (I) 305 has a visible light transmittance of 40% or more). Further, the charge generation layer (I) 305 functions even if it has lower conductivity than the first electrode 301 or the second electrode 304.

The charge generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine such as NPB, TPD, TDATA, MTDATA, or 4,4'-bis[N-(Spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. Note that any substance other than the above substances may be used as long as they are organic compounds with a hole-transport property higher than an electron-transport property.

Further, as the electron acceptor, 7,7,8,8-tetracyano-2,3,5,6-tetrafluoroquinodimethane (abbreviation: $F_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air, has a low hygroscopic property, and is easily handled.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, BPhen, BCP, or the like. The substances mentioned here are mainly ones that have an electron mobility of $10^{-6}$ cm$^2$/Vs or higher. Note that any substance other than the above substances may be used as long as they are organic compounds with an electron-transport property higher than a hole-transport property.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer (I) 305 by using any of the above materials can suppress an increase in drive voltage caused by the stack of the EL layers.

Figure 3B:
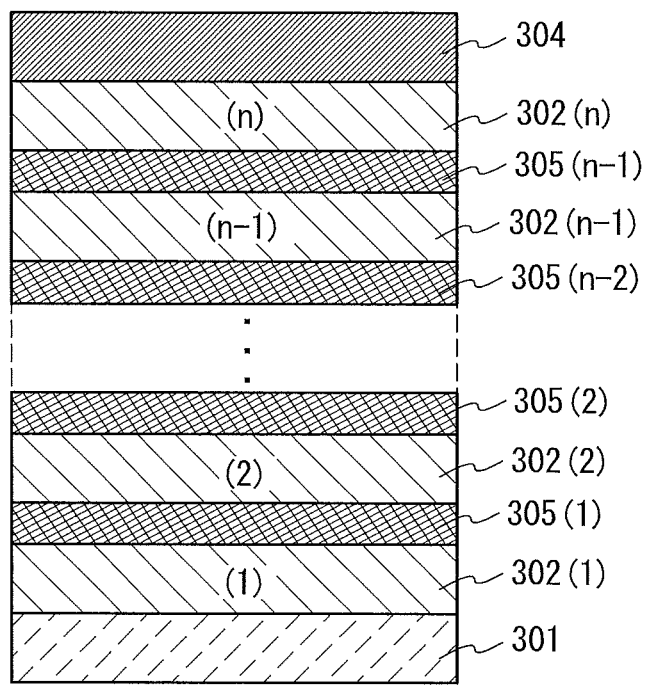

Although this embodiment shows the light-emitting element having two EL layers, the present invention can be similarly applied to a light-emitting element in which n EL layers (302(1) to 302(n)) (n is three or more) are stacked as illustrated in FIG. 3B. In the case where a plurality of EL layers are included between a pair of electrodes as in the light-emitting element according to this embodiment, by providing charge generation layers (I) (305(1) to 305(n−1)) between the EL layers, light emission in a high luminance region can be obtained with current density kept low. Since the current density can be kept low, the element can have a long lifetime. Further, when the light-emitting element is applied to light-emitting devices, electronic devices, and lighting devices each having a large light-emitting area, lighting devices, a voltage drop due to resistance of an electrode material can be reduced and accordingly homogeneous light emission in a large area is possible.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when light obtained from a light-emitting substance and light of a complementary color are mixed, white light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

(Embodiment 5)

In this embodiment, a light-emitting device including a light-emitting element in which the organometallic iridium complex of one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 4A and 4B.

Figure 4A:
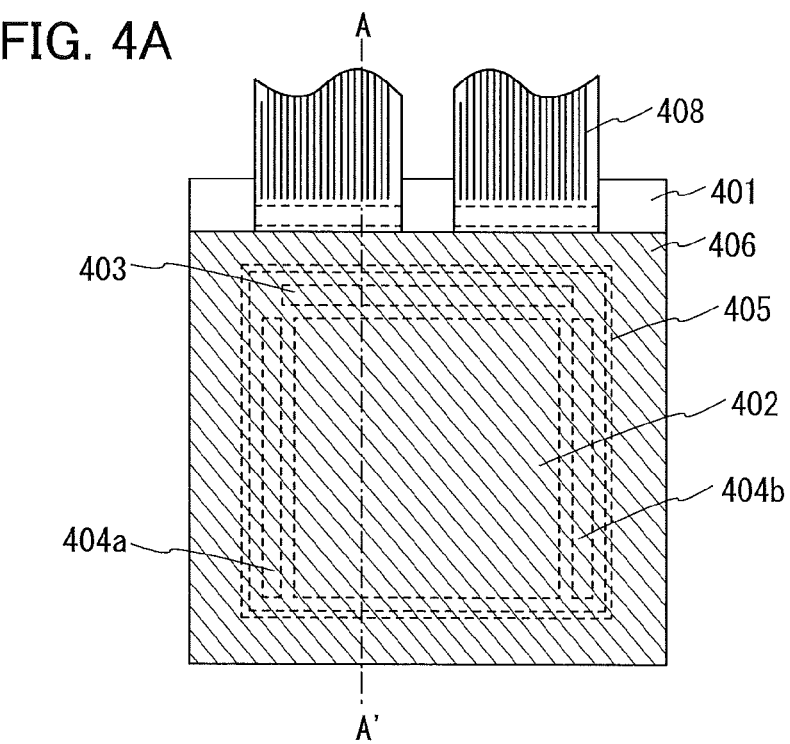
FIGS. 4A and 4B illustrate a light-emitting device.
Figure 4B:
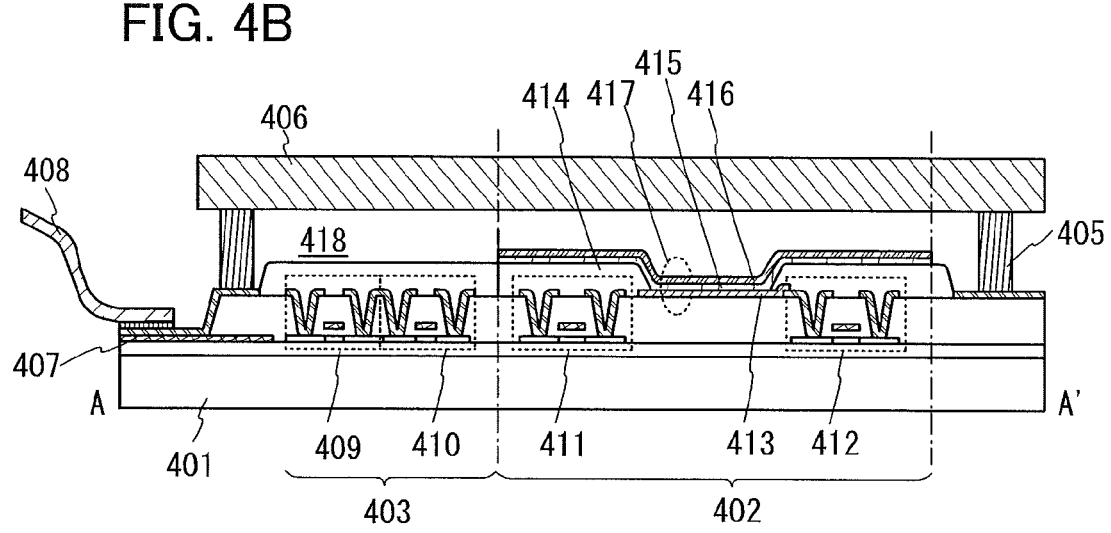

Note that FIG. 4A is a top view illustrating a light-emitting device and FIG. 4B is a cross-sectional view taken along the chain line A-A' in FIG. 4A. The active matrix light-emitting device according to this embodiment includes a pixel portion 402 provided over an element substrate 401, a driver circuit portion (a source line driver circuit) 403, and driver circuit portions (gate line driver circuits) 404 (404a and 404b). The pixel portion 402, the driver circuit portion 403, and the driver circuit portions 404 are sealed between the element substrate 401 and the sealing substrate 406 with a sealant 405.

In addition, a lead wiring 407 is provided over the element substrate 401. The lead wiring 407 is provided for connecting an external input terminal through which a signal (e.g., a video signal, a clock signal, a start signal, and a reset signal) or a potential from the outside is transmitted to the driver circuit portion 403 and the driver circuit portions 404. Here is shown an example in which a flexible printed circuit (FPC) 408 is provided as the external input terminal. Although the FPC 408 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 4B. The driver circuit portion and the pixel portion are formed over the element substrate 401; here are illustrated the driver circuit portion 403 which is the source line driver circuit and the pixel portion 402.

The driver circuit portion 403 is an example where a CMOS circuit is formed, which is a combination of an n-channel TFT 409 and a p-channel TFT 410. Note that a circuit included in the driver circuit portion may be formed using various CMOS circuits, PMOS circuits, or NMOS circuits. Any of a staggered type FET and a reverse-staggered type FET can be used. The crystallinity of a semiconductor film used in the FET is not limited and can be amorphous or crystalline. Examples of a semiconductor material include Group IV semiconductors (e.g., silicon and gallium), compound semiconductors (including oxide semiconductors), and organic semiconductors. Although this embodiment shows a driver integrated type in which the driver circuit is formed over the substrate, the driver circuit is not necessarily formed over the substrate, and may be formed outside the substrate.

The pixel portion 402 is formed of a plurality of pixels each of which includes a switching TFT 411, a current control TFT 412, and a first electrode (anode) 413 which is electrically connected to a wiring (a source electrode or a drain electrode) of the current control TFT 412. Note that an insulator 414 is formed to cover end portions of the first electrode (anode) 413. In this embodiment, the insulator 414 is formed using a positive photosensitive acrylic resin.

The insulator 414 preferably has a curved surface with curvature at an upper end portion or a lower end portion thereof in order to obtain favorable coverage by a film which is to be stacked over the insulator 414. The insulator 414 can be formed using either a negative photosensitive resin or a positive photosensitive resin. The material of the insulator 414 is not limited to an organic compound and an inorganic compound such as silicon oxide or silicon oxynitride can also be used.

An EL layer 415 and a second electrode (cathode) 416 are stacked over the first electrode (anode) 413. In the EL layer 415, at least a light-emitting layer is provided which contains the organometallic iridium complex of one embodiment of the present invention. Further, in the EL layer 415, a hole-injection layer, a hole-transport layer, an electron-transport layer, an electron-injection layer, a charge generation layer, and the like can be provided as appropriate in addition to the light-emitting layer.

A light-emitting element 417 is formed of a stacked structure of the first electrode (anode) 413, the EL layer 415, and the second electrode (cathode) 416. For the first electrode (anode) 413, the EL layer 415, and the second electrode (cathode) 416, the materials described in Embodiment 2 can be used. Although not illustrated, the second electrode (cathode) 416 is electrically connected to the FPC 408 which is an external input terminal.

Although the cross-sectional view of FIG. 4B illustrates only one light-emitting element 417, a plurality of light-emitting elements are arranged in matrix in the pixel portion 402. Light-emitting elements which provide three kinds of light emission (R, G, and B) are selectively formed in the pixel portion 402, whereby a light-emitting device capable of full color display can be fabricated. Alternatively, a light-emitting device which is capable of full color display may be fabricated by a combination with color filters.

Further, the sealing substrate 406 is attached to the element substrate 401 with the sealant 405, whereby the light-emitting element 417 is provided in a space 418 surrounded by the element substrate 401, the sealing substrate 406, and the sealant 405. The space 418 may be filled with an inert gas (such as nitrogen or argon), or the sealant 405.

An epoxy-based resin is preferably used for the sealant 405. It is preferable that such a material do not transmit moisture or oxygen as much as possible. As the sealing substrate 406, a glass substrate, a quartz substrate, or a plastic substrate formed of fiberglass reinforced plastic (FRP), poly(vinyl fluoride) (PVF), polyester, acrylic, or the like can be used. In the case where glass frit is used as the sealant, the element substrate 401 and the sealing substrate 406 are preferably glass substrates in terms of adhesion.

As described above, an active matrix light-emitting device can be obtained.

Note that the structure described in this embodiment can be combined as appropriate with any of the structures described in the other embodiments.

(Embodiment 6)

In this embodiment, examples of a variety of electronic devices which are completed using a light-emitting device are described with reference to FIGS. 5A to 5D. To the light-emitting device, the light-emitting element of one embodiment of the present invention is applied.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 5A to 5D.

Figure 5A:
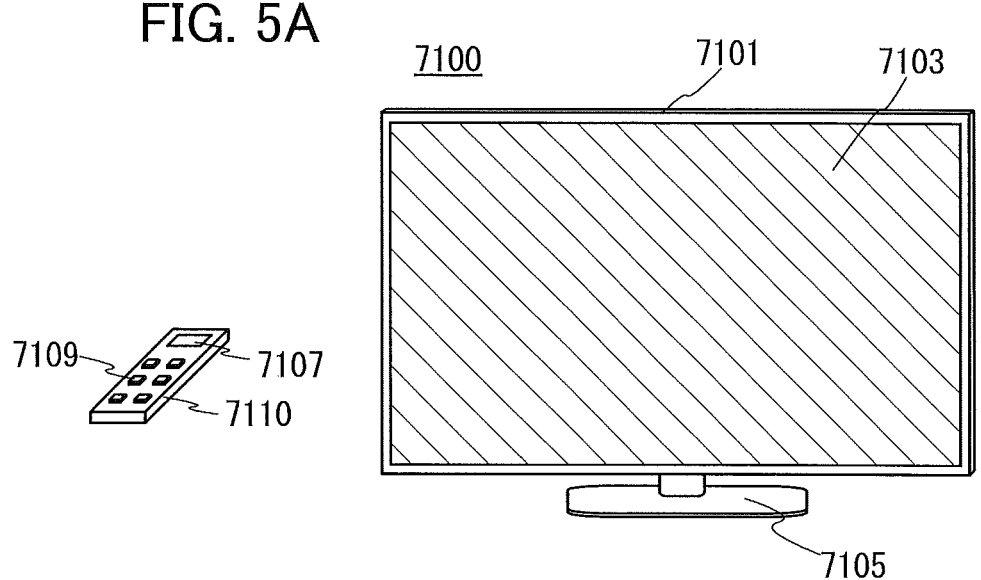
FIGS. 5A to 5D illustrate electronic devices.

FIG. 5A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 5B:
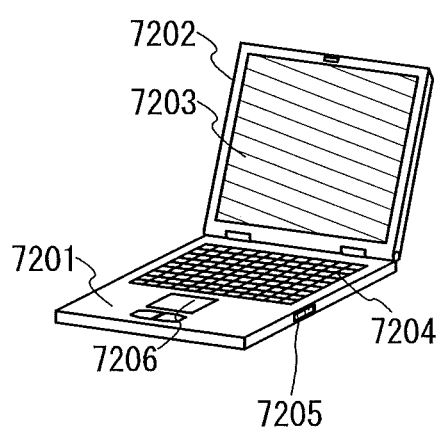

FIG. 5B illustrates a computer having a main body 7201, a housing 7202, a display portion 7203, a keyboard 7204, an external connection port 7205, a pointing device 7206, and the like. Note that this computer can be manufactured using the light-emitting device for the display portion 7203.

Figure 5C:
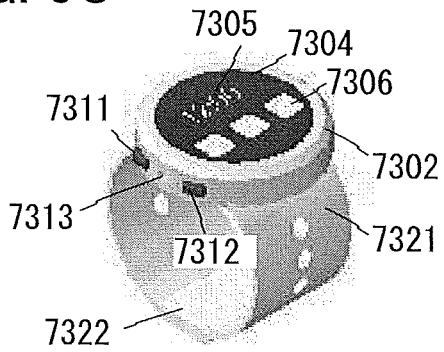

FIG. 5C illustrates a smart watch. The smart watch includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like.

The smart watch in FIG. 5C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 5D:
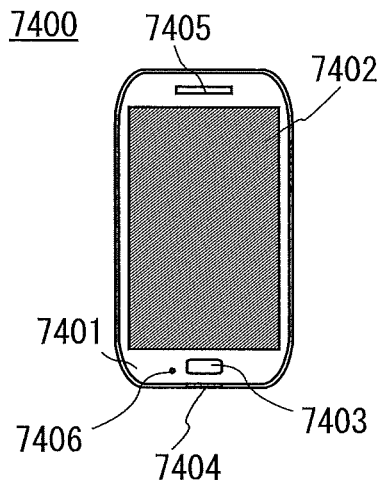

FIG. 5D illustrates an example of a mobile phone. A mobile phone 7400 is provided with a display portion 7402 incorporated in a housing 7401, an operation buttons 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 5D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation button 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained by application of the light-emitting device of one embodiment of the present invention. The light-emitting device has a remarkably wide application range, and can be applied to electronic devices in a variety of fields.

Note that the structure described in this embodiment can be combined as appropriate with any of the structures described in the other embodiments.

(Embodiment 7)

In this embodiment, examples of a lighting device to which a light-emitting device including the organometallic iridium complex of one embodiment of the present invention is applied are described with reference to FIG. 6.

Figure 6:
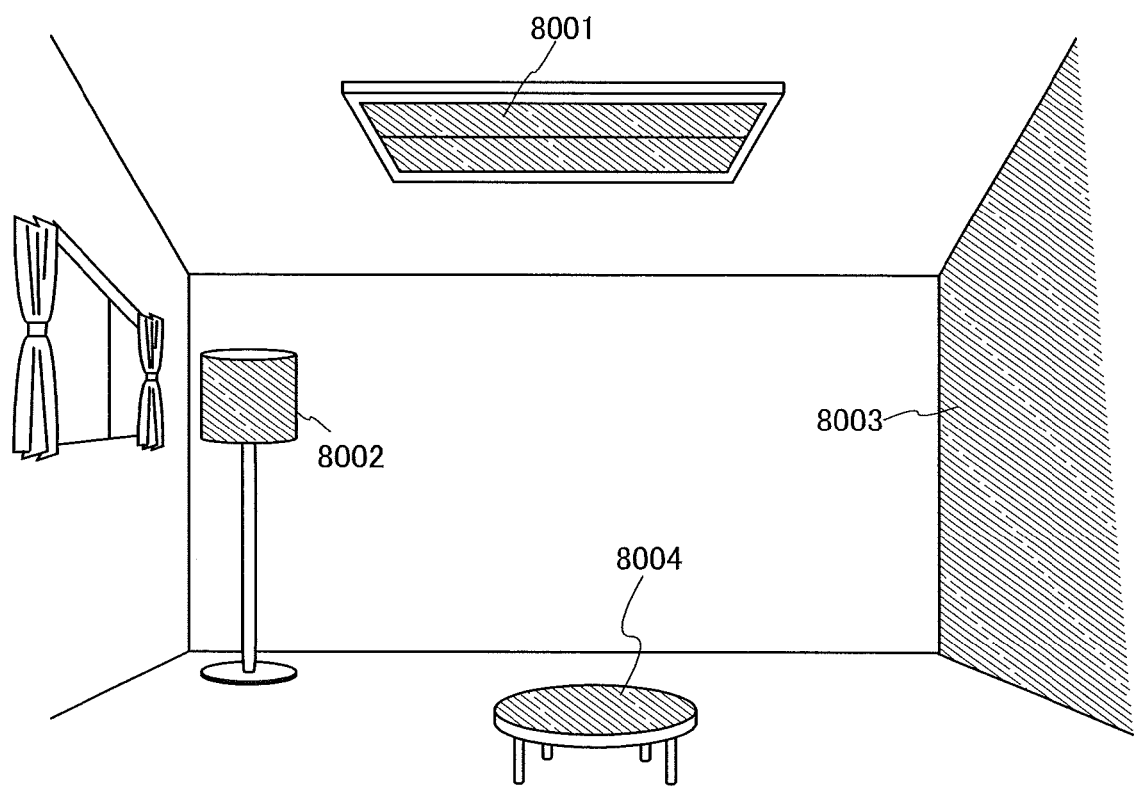
FIG. 6 illustrates lighting devices.

FIG. 6 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

EXAMPLE 1

SYNTHESIS EXAMPLE 1

In this example, a method for synthesizing bis{2-[6-(2,6-dimethylphenyl)-4-pyrimidinyl-κN3]phenyl-κC}(2,4-pentanedionato-κO,O')iridium(III) (abbreviation: [Ir(ppm-dmp)$_2$ (acac)]), which is an organometallic iridium complex of one embodiment of the present invention represented by Structural Formula (100) in Embodiment 1, is described. The structure of [Ir(ppm-dmp)$_2$(acac)] is shown below.

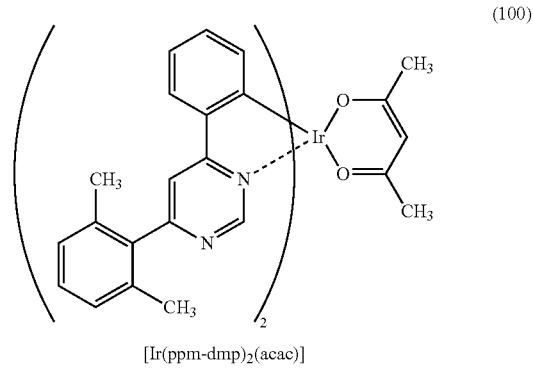

[Ir(ppm-dmp)$_2$(acac)]

<Step 1: Synthesis of 4-chloro-6-phenylpyrimidine>

First, 5.0 g of 4,6-dichloropyrimidine, 4.9 g of phenylboronic acid, 7.1 g of sodium carbonate, 0.34 g of bis(triphenylphosphine)palladium(II) dichloride (abbreviation: PdCl$_2$(PPh)$_2$), 20 mL of acetonitrile, and 20 mL of water were put into a 100-mL round-bottom flask equipped with a reflux pipe, and the atmosphere in the flask was replaced with argon. Then, heating was performed by irradiation with microwaves (2.45 GHz, 100 W) for 1 hour. An organic layer was extracted from the obtained mixture with the use of dichloromethane. The organic layer was washed with water and saturated saline and dried over magnesium sulfate. The mixture was subjected to gravity filtration. The solvent in the obtained filtrate was distilled off, and the given residue was purified by flash column chromatography using dichloromethane as a developing solvent, whereby 1.6 g of the objective substance was obtained (yield: 23%, a pale yellow solid). Note that the irradiation with microwaves was performed using a microwave synthesis system (Discover, manufactured by CEM Corporation). Synthesis Scheme (a-1) of Step 1 is shown below.

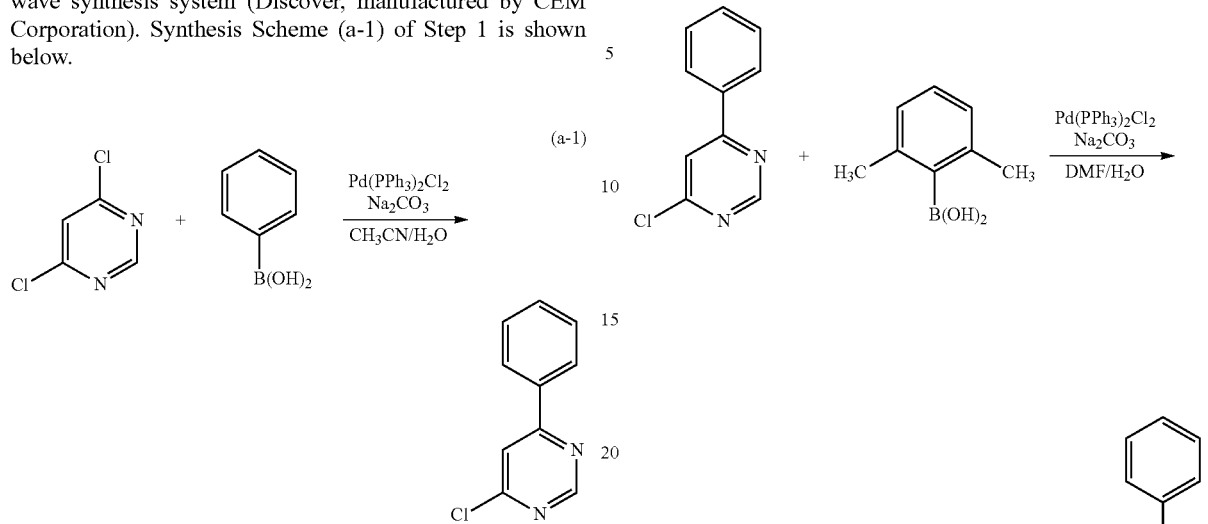

(a-1)

<Step 2: Synthesis of 4-phenyl-6-(2,6-dimethylphenyl)pyrimidine (abbreviation: Hppm-dmp)>

Next, 1.6 g of 4-chloro-6-phenylpyrimidine synthesized in Step 1, 1.5 g of 2,6-dimethylphenylboronic acid, 1.8 g of sodium carbonate, 59 mg of PdCl$_2$(PPh)$_2$, 20 mL of N,N-dimethylformamide (abbreviation: DMF), and 20 mL of water were put into a 100-mL round-bottom flask, and the atmosphere in the flask was replaced with argon. Then, heating was performed by irradiation with microwaves (2.45 GHz, 100 W) for 2 hours. An organic layer was extracted from the obtained mixture with the use of dichloromethane. The organic layer was washed with water and saturated saline and dried over magnesium sulfate. The mixture was subjected to gravity filtration. A solvent in the obtained filtrate was distilled off, and the given residue was purified by flash column chromatography using a mixed solvent of ethyl acetate and hexane (ethyl acetate:hexane=1:5) as a developing solvent, whereby 0.50 g of the objective substance, Hppm-dmp was obtained (yield: 23%, a pale yellow oily substance). Synthesis Scheme (a-2) of Step 2 is shown below.

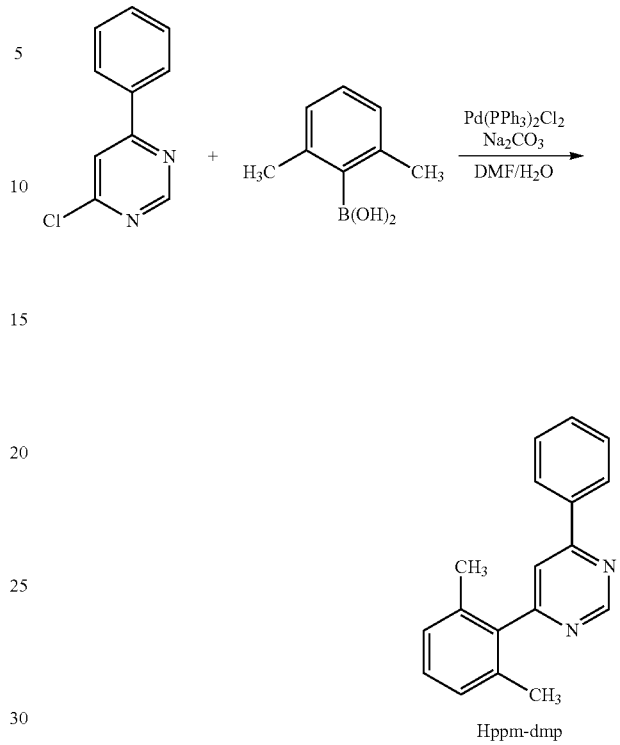

(a-2)

<Step 3: Synthesis of di-μ-chloro-tetrakis{2-[6-(2,6-dimethylphenyl)-4-pyrimidinyl-κN3]phenyl-κC}diiridium(III) (abbreviation: [Ir(ppm-dmp)$_2$Cl]$_2$)>

Into a 100-mL round-bottom flask were put 1.0 g of Hppm-dmp synthesized in Step 2, 0.57 g of iridium(III) chloride hydrate, 20 mL of 2-ethoxyethanol, and 20 mL of water, and the atmosphere in the flask was replaced with argon. Then, heating was performed by irradiation with microwaves (2.45 GHz, 100 W) for 3 hours. The obtained mixture was suction-filtered using methanol, whereby 1.1 g of the objective substance, [Ir(ppm-dmp)$_2$Cl]$_2$ was obtained (yield: 74%, an orange solid). Synthesis Scheme (a-3) of Step 3 is shown below.

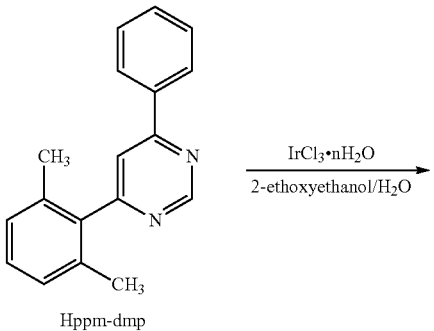

(a-3)

-continued

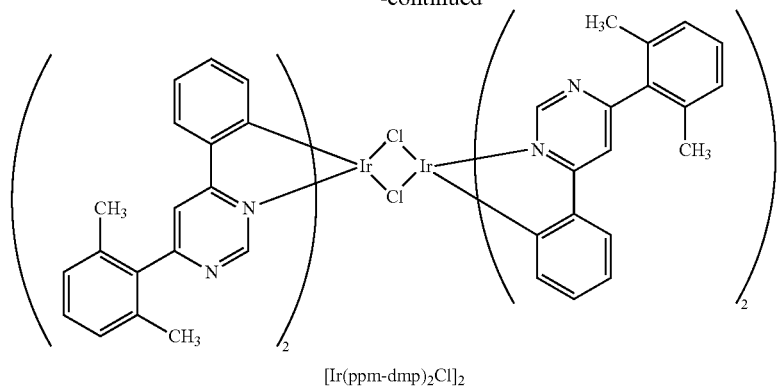

[Ir(ppm-dmp)₂Cl]₂

<Step 4: Synthesis of bis{2-[6-(2,6-dimethylphenyl)-4-pyrimidinyl-κN3]phenyl-κC}(2,4-pentanedionato-κO,O')iridium(III) (abbreviation: [Ir(ppm-dmp)₂(acac)])>

Into a 100-mL round-bottom flask equipped with a reflux pipe were put 1.1 g of [Ir(ppm-dmp)₂Cl]₂ synthesized in Step 3, 0.77 g of sodium carbonate, 0.23 g of acetylacetone (abbreviation: Hacac), and 30 mL of 2-ethoxyethanol, and the atmosphere in the flask was replaced with argon. Then, heating was performed by irradiation with microwaves (2.45 GHz, 120 W) for 2 hours. The obtained mixture was suction-filtrated using methanol, and a solvent of the filtrate was distilled off.

The obtained residue was purified by flash column chromatography using a mixed solvent of ethyl acetate and hexane (ethyl acetate:hexane=1:5) as a developing solvent, and recrystallization was performed using hexane, whereby an organometallic iridium complex of one embodiment of the present invention, [Ir(ppm-dmp)₂(acac)], was obtained (yield: 59%, an orange powdered solid). By a train sublimation method, 0.21 g of the obtained orange powdered solid was purified. In the purification by sublimation, the solid was heated at 240° C. under a pressure of 2.7 Pa with an argon flow rate of 5.0 mL/min. Thus, an orange solid, which was an objective substance, was obtained in a yield of 48%. Synthesis Scheme (a-4) of Step 4 is shown below.

(a-4)

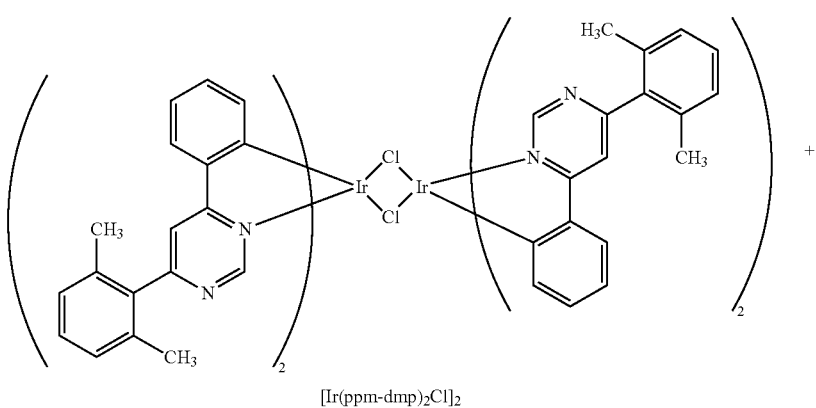

[Ir(ppm-dmp)₂Cl]₂

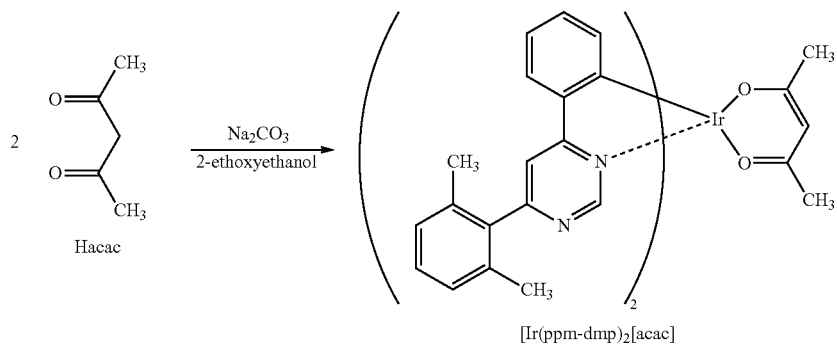

[Ir(ppm-dmp)₂[acac]]

Figure 7:
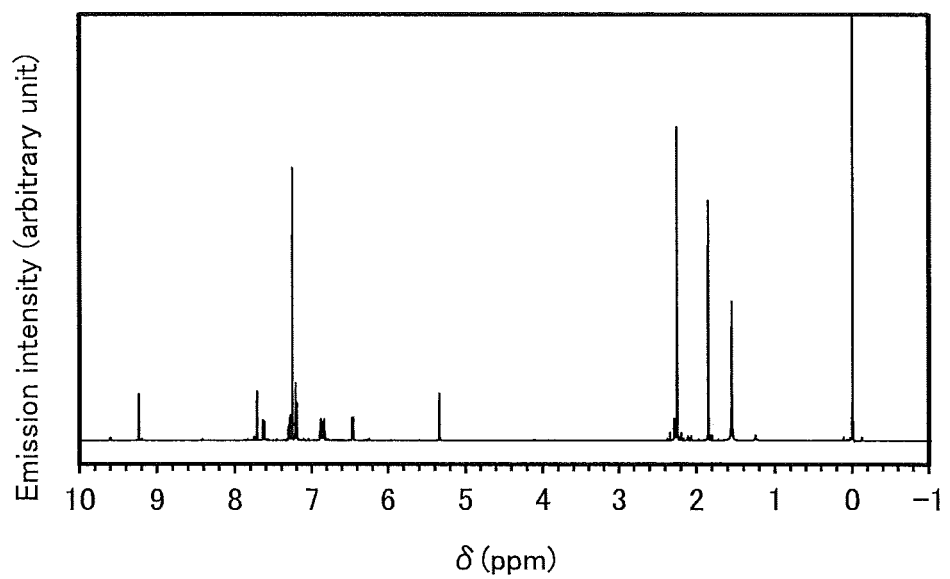
FIG. 7 shows a $^1$H-NMR chart of an organometallic iridium complex represented by Structural Formula (100).

An analysis result by nuclear magnetic resonance spectrometry ($^1$H-NMR) of the orange solid obtained in Step 4 is described below. The $^1$H NMR chart is shown in FIG. 7. This result reveals that [Ir(ppm-dmp)$_2$(acac)], which is the organometallic iridium complex of one embodiment of the present invention represented by Structural Formula (100), was obtained in Synthesis Example 1.

$^1$H-NMR. δ (CDCl$_3$): 1.85 (s, 6H), 2.26 (s, 12H), 5.35 (s, 1H), 6.46-6.48 (dd, 2H), 6.83-6.90 (dm, 4H), 7.20-7.22 (d, 4H), 7.29-7.32 (t, 2H), 7.63-7.65 (dd, 2H), 7.72 (ds, 2H), 9.24 (ds, 2H).

Figure 8:
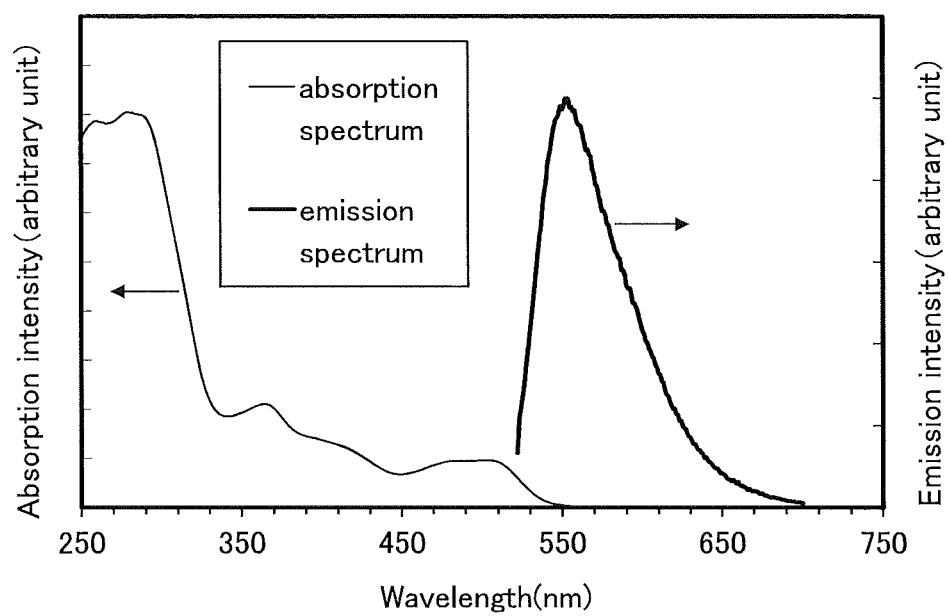
FIG. 8 shows an ultraviolet-visible absorption spectrum and an emission spectrum of the organometallic iridium complex represented by Structural Formula (100).

Next, an ultraviolet-visible absorption spectrum (hereinafter, simply referred to as an "absorption spectrum") of a dichloromethane solution of [Ir(ppm-dmp)$_2$(acac)] and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.090 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed dichloromethane solution (0.090 mmol/L) was put in a quartz cell. Measurement results of the obtained absorption and emission spectra are shown in FIG. 8, in which the horizontal axis represents wavelength and the vertical axes represent absorption intensity and emission intensity. In FIG. 8 where there are two solid lines, the thin line represents the absorption spectrum and the thick line represents the emission spectrum. Note that the absorption spectrum in FIG. 8 is the results obtained in such a way that the absorption spectrum measured by putting only dichloromethane in a quartz cell was subtracted from the absorption spectrum measured by putting the dichloromethane solution (0.090 mmol/L) in a quartz cell.

As shown in FIG. 8, [Ir(ppm-dmp)$_2$(acac)], the organometallic iridium complex of one embodiment of the present invention, has an emission peak at approximately 553 nm, and yellow light emission was observed from the dichloromethane solution.

EXAMPLE 2

Figure 9:
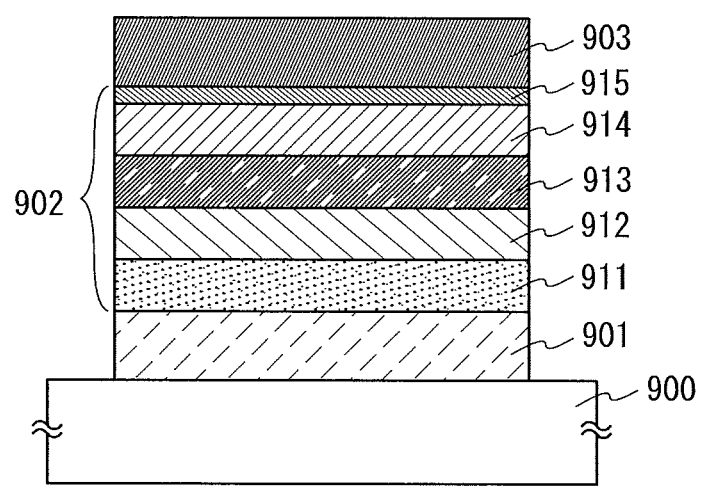
FIG. 9 illustrates a light-emitting element.

In this example, Light-emitting Element 1 and Comparative Light-emitting Element 2 were fabricated and emission spectra of these elements were measured. For a light-emitting layer of Light-emitting Element 1, [Ir(ppm-dmp)$_2$(acac)], which is the organometallic iridium complex of one embodiment of the present invention represented by Structural Formula (100), was used. For a light-emitting layer of Comparative Light-emitting Element 2, [Ir(mpmppm)$_2$(acac)], which is an organometallic iridium complex, was used. Note that fabrication of Light-emitting Element 1 and Comparative Light-emitting Element 2 are described with reference to FIG. 9. Chemical formulae of materials used in this example are shown below.

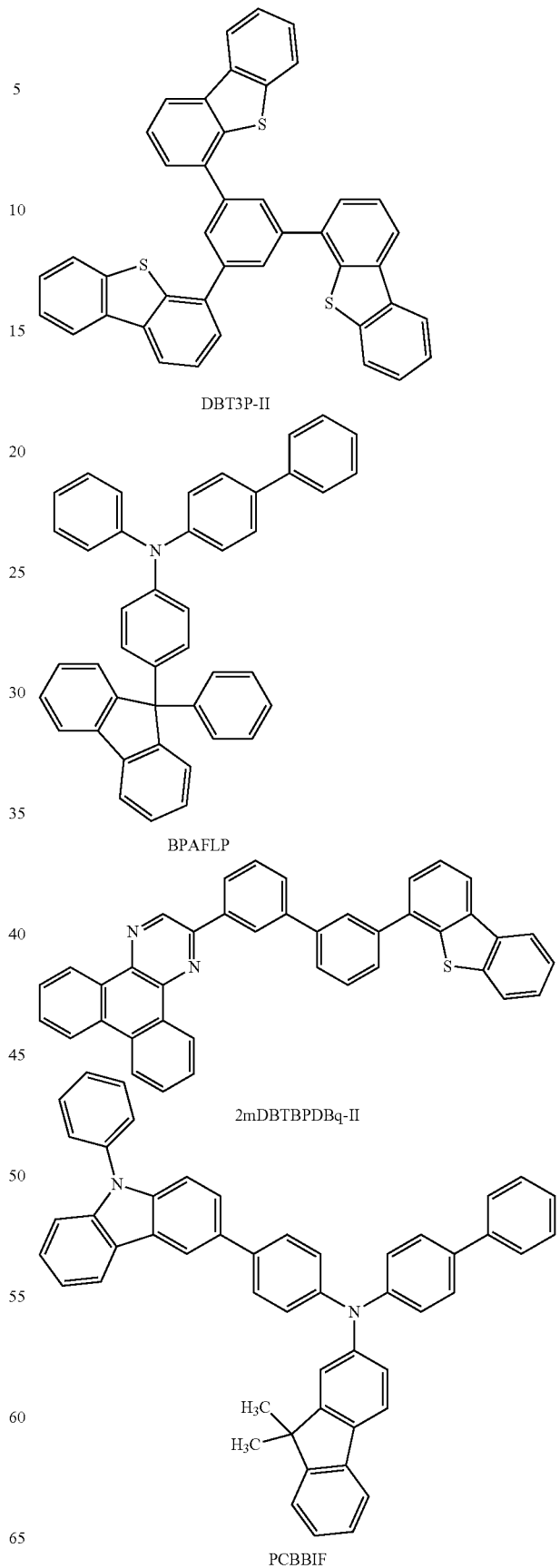

DBT3P-II

BPAFLP

2mDBTBPDBq-II

PCBBiF

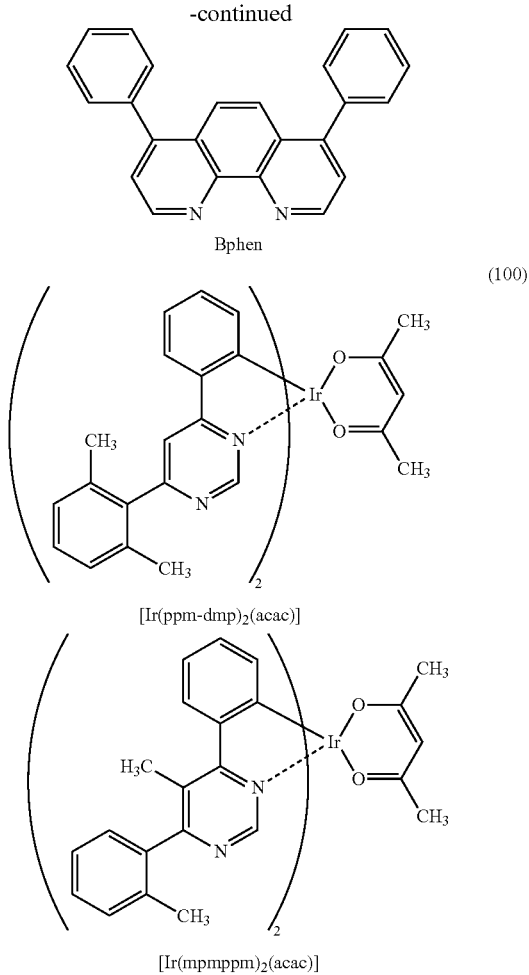

<<Fabrication of Light-Emitting Element 1 and Comparative Light-Emitting Element 2>>

First, indium tin oxide containing silicon oxide (ITSO) was deposited over a glass substrate 900 by a sputtering method, so that a first electrode 901 which functions as an anode was formed. The thickness was 110 nm and the electrode area was 2 mm×2 mm.

Then, as pretreatment for forming Light-emitting Element 1 and Comparative Light-emitting Element 2 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 900 was cooled down for about 30 minutes.

Next, the substrate 900 was fixed to a holder provided in the vacuum evaporation apparatus so that a surface of the substrate 900 over which the first electrode 901 was formed faced downward. In this example, a case will be described in which a hole-injection layer 911, a hole-transport layer 912, a light-emitting layer 913, an electron-transport layer 914, and an electron-injection layer 915 which are included in an EL layer 902 are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 911 was formed over the first electrode 901. The thickness of the hole-injection layer 911 was 20 nm. Note that the co-evaporation is an evaporation method in which some different substances are evaporated from some different evaporation sources at the same time.

Then, 4-phenyl-4'-(9-phenylfluoren-9-yl)triphenylamine (abbreviation: BPAFLP) was deposited by evaporation to a thickness of 20 nm, so that the hole-transport layer 912 was formed.

Next, the light-emitting layer 913 was formed over the hole-transport layer 912. In the case of Light-emitting Element 1, co-deposited by evaporation were 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-9,9-dimethyl-N-[4-(9-phenyl-9H-carbazol-3-yl)phenyl]-9H-fluoren-2-amine (abbreviation: PCBBiF), and [Ir(ppm-dmp)$_2$(acac)] with a mass ratio of 2mDBTBPDBq-II to PCBBiF and [Ir(ppm-dmp)$_2$(acac)] being 0.8:0.2:0.05. The thickness of the light-emitting layer 913 was 40 nm.

In the case of Comparative Light-emitting Element 2, co-deposited by evaporation were 2mDBTBPDBq-II, PCBBiF, and bis{2-[5-methyl-6-(2-methylphenyl)-4-pyrimidinyl-κN3]phenyl-κC}(2,4-pentanedionato-κ$^2$O,O')iridium(III) (abbreviation: [Ir(mpmppm)$_2$(acac)]) with a mass ratio of 2mDBTBPDBq-II to PCBBiF and [Ir(mpmppm)$_2$(acac)] being 0.8:0.2:0.05. The thickness of the light-emitting layer 913 was 40 nm.

Then, over the light-emitting layer 913, 2mDBTBPDBq-II was deposited by evaporation to a thickness of 15 nm and then bathophenanthroline (abbreviation: Bphen) was deposited by evaporation to a thickness of 10 nm, whereby the electron-transport layer 914 was formed. Furthermore, lithium fluoride was deposited by evaporation to a thickness of 1 nm over the electron-transport layer 914, whereby the electron-injection layer 915 was formed.

Finally, aluminum was deposited by evaporation to a thickness of 200 nm over the electron-injection layer 915 to form a second electrode 903 serving as a cathode; thus, Light-emitting Element 1 and Comparative Light-emitting Element 2 were obtained. Note that in all the above evaporation steps, evaporation was performed by a resistance-heating method.

Element structures of Light-emitting Element 1 and Comparative Light-emitting Element 2 obtained as described above are shown in Table 1.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting | ITSO (110 nm) | DBT3P-II:MoOx (4:2 | BPAFLP (20 nm) | * | 2mDBTBPDBq-II (15 nm) | Bphen (10 nm) | LiF (1 nm) | Al (200 nm) |

TABLE 1-continued

| | First electrode | Hole-injection layer | Hole-transport layer | Light-emitting layer | Electron-transport layer | | Electron-injection layer | Second electrode |
|---|---|---|---|---|---|---|---|---|
| Element 1 Comparative Light-emitting Element 2 | ITSO (110 nm) | 20 nm) DBT3P-II:MoOx (4:2 20 nm) | BPAFLP (20 nm) | ** | 2mDBTBPDBq-II (15 nm) | Bphen (10 nm) | LiF (1 nm) | Al (200 nm) |

\* 2mDBTBPDBq-II:PCBBiF:[Ir(ppm-dmp)$_2$(acac)] (0.8:0.2:0.05 40 nm)
\*\* 2mDBTBPDBq-II:PCBBiF:[Ir(mpmppm)$_2$(acac)] (0.8:0.2:0.05 40 nm)

Further, each of the fabricated Light-emitting Element 1 and Comparative Light-emitting Element 2 was sealed in a glove box containing a nitrogen atmosphere so as not to be exposed to the air (specifically, a sealant was applied onto an outer edge of the element and heat treatment was performed at 80° C. for 1 hour at the time of sealing).

<<Operation Characteristics of Light-emitting Element 1 and Comparative Light-emitting Element 2>>

Operation characteristics of Light-emitting Element 1 and Comparative Light-emitting Element 2 were measured. Note that the measurement was carried out at room temperature (under an atmosphere in which the temperature was kept at 25° C.).

Figure 10:
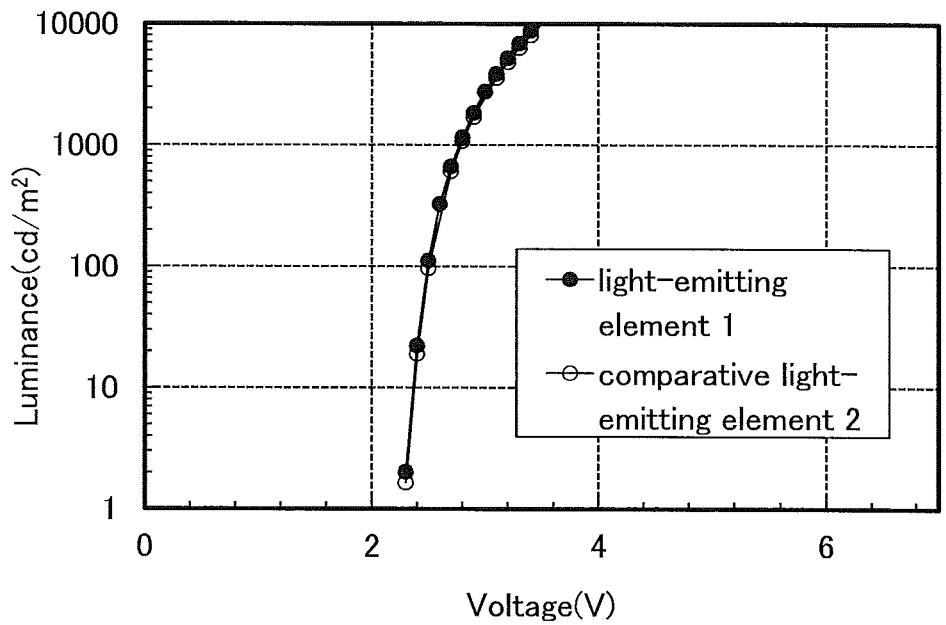
FIG. 10 shows luminance vs. voltage characteristics of Light-emitting Element 1 and Comparative Light-emitting Element 2.
Figure 11:
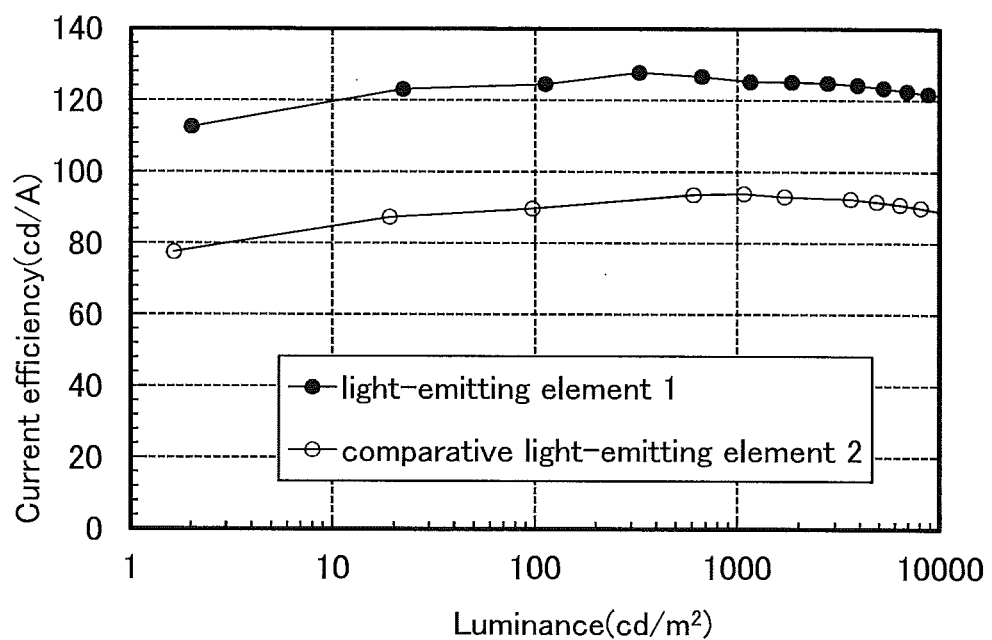
FIG. 11 shows current efficiency vs. luminance characteristics of Light-emitting Element 1 and Comparative Light-emitting Element 2.
Figure 12:
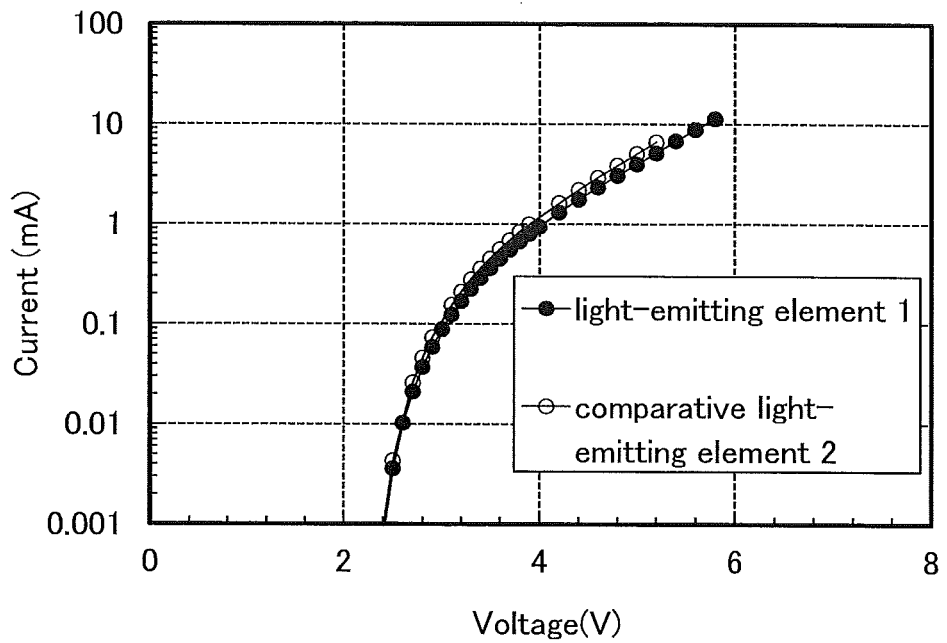
FIG. 12 shows current vs. voltage characteristics of Light-emitting Element 1 and Comparative Light-emitting Element 2.
Figure 13:
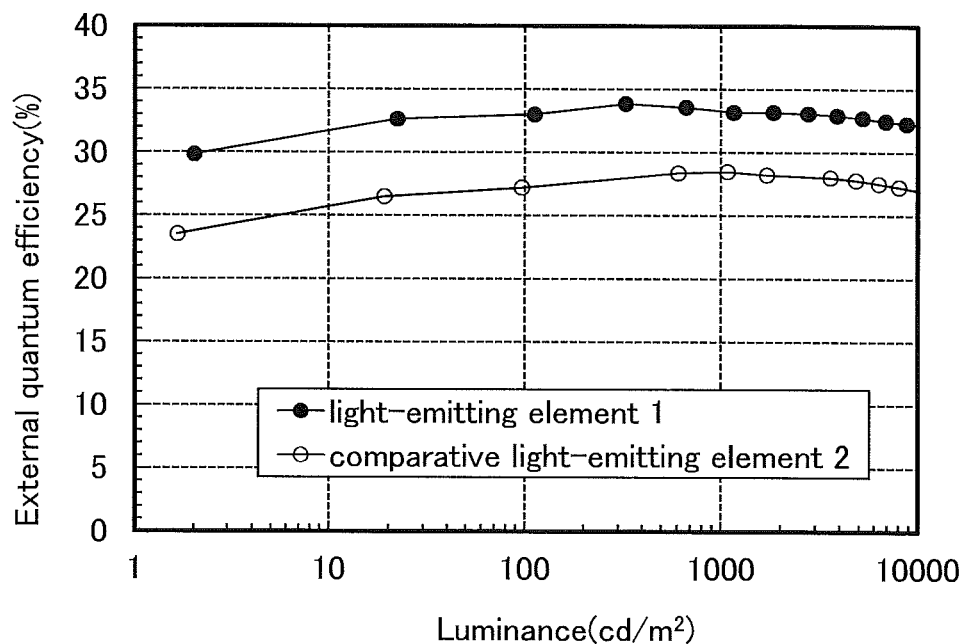
FIG. 13 shows external quantum efficiency vs. luminance characteristics of Light-emitting Element 1 and Comparative Light-emitting Element 2.

FIG. 10 shows voltage-luminance characteristics of Light-emitting Element 1 and Comparative Light-emitting Element 2. In FIG. 10, the vertical axis represents luminance (cd/m$^2$) and the horizontal axis represents voltage (V). Further, FIG. 11 shows luminance-current efficiency characteristics of Light-emitting Element 1 and Comparative Light-emitting Element 2. In FIG. 11, the vertical axis represents current efficiency (cd/A) and the horizontal axis represents luminance (cd/m$^2$). FIG. 12 shows voltage-current characteristics of Light-emitting Element 1 and Comparative Light-emitting Element 2. In FIG. 12, the vertical axis represents current (mA) and the horizontal axis represents voltage (V). In addition, FIG. 13 shows luminance-external quantum efficiency characteristics of Light-emitting Element 1 and Comparative Light-emitting Element 2. In FIG. 13, the vertical axis represents external quantum efficiency (%) and the horizontal axis represents luminance (cd/m$^2$).

FIG. 11 and FIG. 13 reveal high efficiency of Light-emitting Element 1 of one embodiment of the present invention. Table 2 shows initial values of main characteristics of Light-emitting Element 1 and Comparative Light-emitting Element 2 at a luminance of about 1000 cd/m$^2$.

Figure 14:
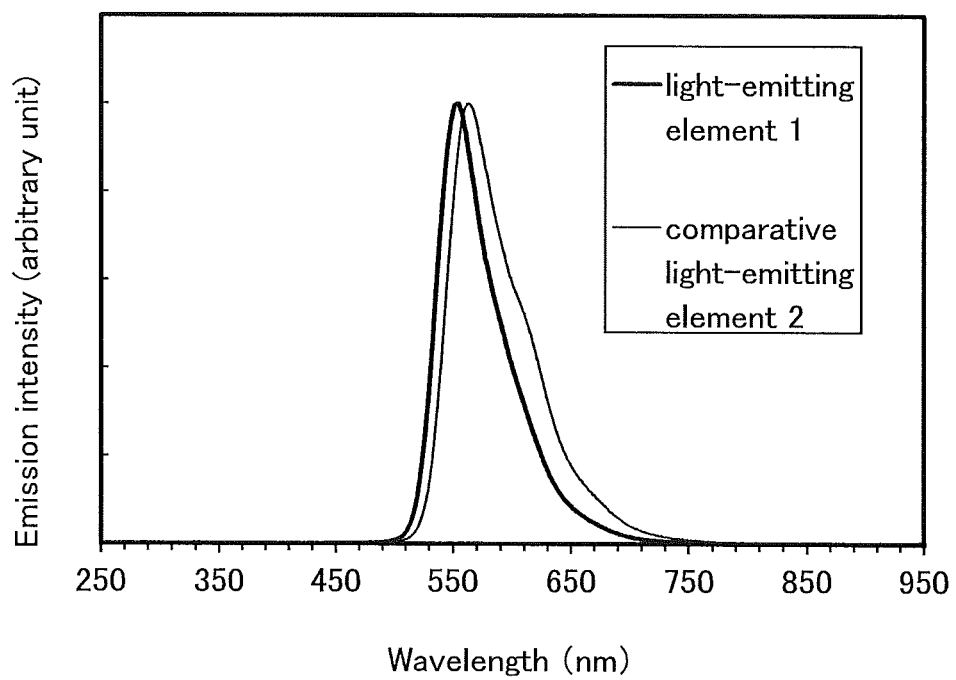
FIG. 14 shows emission spectra of Light-emitting Element 1 and Comparative Light-emitting Element 2.

FIG. 14 shows emission spectra when a current at a current density of 25 mA/cm$^2$ was supplied to Light-emitting Element 1 and Comparative Light-emitting Element 2. As shown in FIG. 14, the emission spectrum of Light-emitting Element 1 has a peak at approximately 557 nm, which indicates that the peak was derived from emission from [Ir(ppm-dmp)$_2$(acac)], which is an organometallic iridium complex of one embodiment of the present invention. In Comparative Light-emitting Element 2, the organometallic iridium complex [Ir(mpmppm)$_2$(acac)] was used instead of the organometallic iridium complex [Ir(ppm-dmp)$_2$(acac)] of Light-emitting Element 1. It was observed that the half width of the emission spectrum of Light-emitting Element 1 is smaller than that of the emission spectrum of Comparative Light-emitting Element 2. This can be presumed to be an effect brought about by the structure of the organometallic iridium complex [Ir(ppm-dmp)$_2$(acac)] of one embodiment of the present invention, in which a phenyl group whose 2-position and 6-position are each substituted by a methyl group is bonded to iridium. Therefore, it can be said that Light-emitting Element 1 has high emission efficiency and achieves high color purity.

Figure 15:
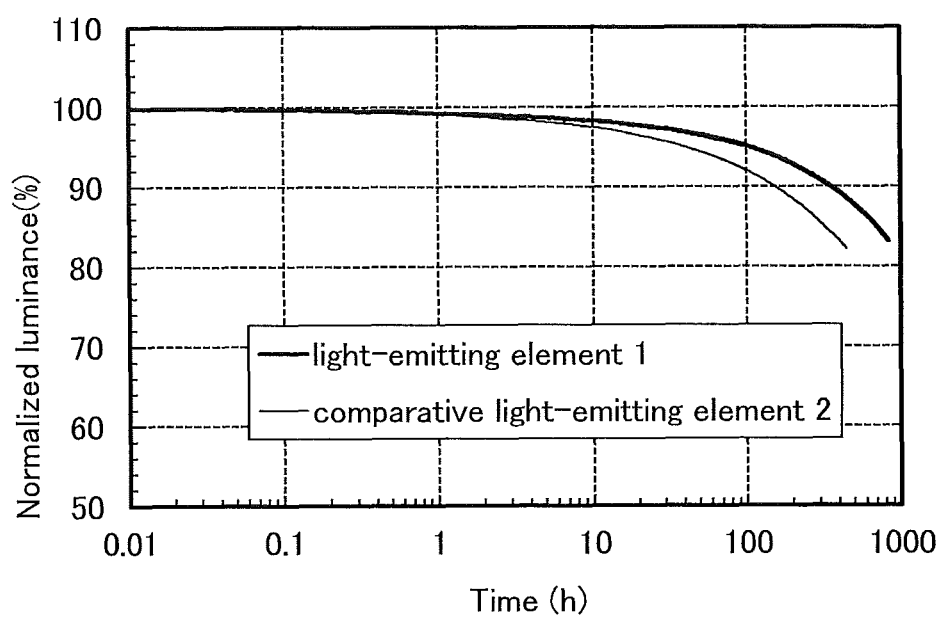
FIG. 15 shows reliability of each of Light-emitting Element 1 and Comparative Light-emitting Element 2.

Light-emitting Element 1 and Comparative Light-emitting Element 2 were subjected to a reliability test. Results of the reliability test are shown in FIG. 15. In FIG. 15, the vertical axis represents normalized luminance (%) with an initial luminance of 100% and the horizontal axis represents driving time (h) of the element. Note that in the reliability test, Light-emitting Element 1 was driven under the conditions where the initial luminance was set to 5000 cd/m$^2$ and the current density was constant. Light-emitting Element 1 kept about 95% of the initial luminance after 100 hours elapsed.

Thus, the reliability test conducted under the above condition showed that Light-emitting Element 1 is highly reliable.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting Element 1 | 2.8 | 0.037 | 0.93 | (0.44, 0.55) | 1200 | 130 | 140 | 33 |
| Comparative Light-emitting Element 2 | 2.8 | 0.046 | 1.2 | (0.49, 0.50) | 1100 | 94 | 110 | 28 |

The above results show that Light-emitting Element 1 fabricated in this example is a high-luminance light-emitting element having high current efficiency. Moreover, as for color purity, it can be found that the light-emitting element exhibits yellow emission with excellent color purity.

In addition, it was confirmed that with the use of the organometallic iridium complex of one embodiment of the present invention, a light-emitting element with a long lifetime can be obtained.

This application is based on Japanese Patent Application serial no. 2013-136143 filed with Japan Patent Office on Jun. 28, 2013, the entire contents of which are hereby incorporated by reference.

What is claimed is:

1. A compound comprising a structure represented by Formula (G1):

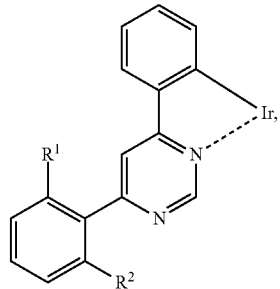
(G1)

wherein $R^1$ and $R^2$ independently represent a substituted or unsubstituted alkyl group having 1 to 6 carbon atoms.

2. A compound represented by Formula (G2):

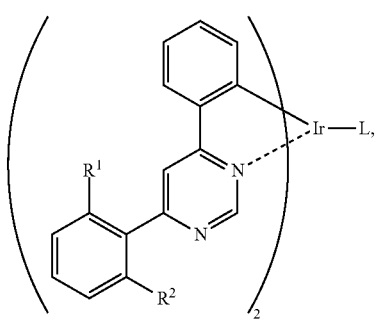
(G2)

wherein $R^1$ and $R^2$ independently represent a substituted or unsubstituted alkyl group having 1 to 6 carbon atoms, and wherein L represents a monoanionic ligand.

3. A compound according to claim 2, wherein the monoanionic ligand is any one of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two coordinating elements are both nitrogen.

4. A compound according to claim 2, wherein the monoanionic ligand is represented by any one of Formulae (L1) to (L7):

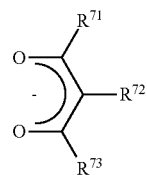
(L1)

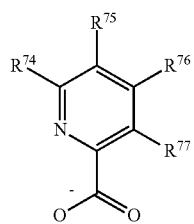
(L2)

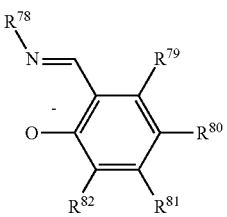
(L3)

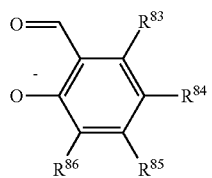
(L4)

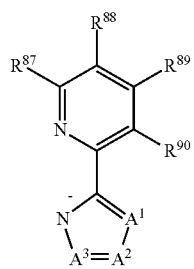
(L5)

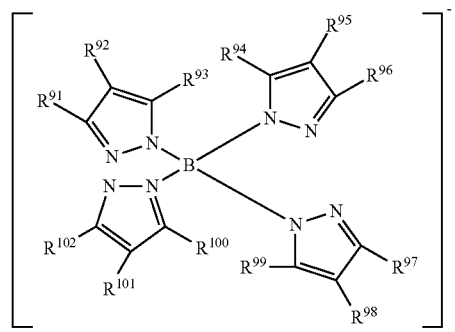
(L6)

-continued (L7)

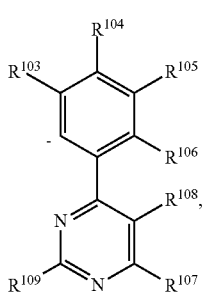

wherein $R^{71}$ to $R^{109}$ individually represent any of hydrogen, a substituted or unsubstituted alkyl group having 1 to 6 carbon atoms, halogen, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms, wherein $A^1$ to $A^3$ individually represent any of nitrogen, $sp^2$ hybridized carbon bonded to hydrogen, and $sp^2$ carbon having a substituent, and wherein the substituent is any of an alkyl group having 1 to 6 carbon atoms, halogen, a haloalkyl group having 1 to 6 carbon atoms, and a phenyl group.

5. A compound represented according to claim 2, wherein the compound is represented by Formula (G3):

(G3)

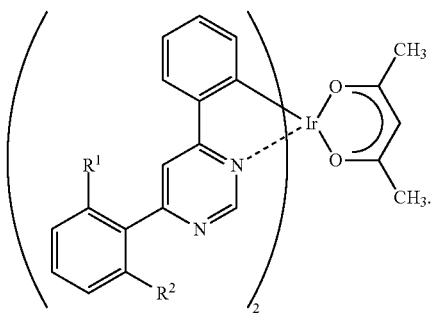

6. A compound according to claim 1, wherein the compound is represented by Formula (G4):

(G4)

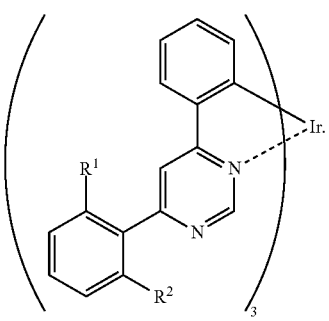

7. A compound according to claim 5, wherein the compound is represented by Formula (100):

(100)

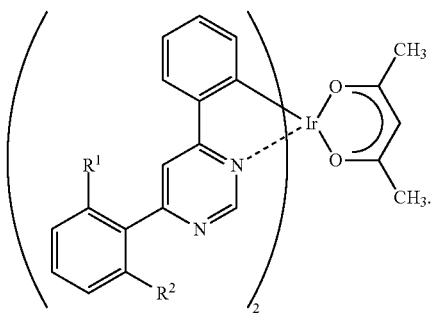

8. A light-emitting element comprising the compound according to claim 1.

9. A light-emitting device comprising the light-emitting element according to claim 8.

10. An electronic device comprising the light-emitting device according to claim 9.

11. A lighting device comprising the light-emitting device according to claim 9.

* * * * *